United States Patent
Chan et al.

(10) Patent No.: US 7,659,275 B2
(45) Date of Patent: Feb. 9, 2010

(54) PIPERIDINYL PIPERAZINE DERIVATIVES USEFUL AS INHIBITORS OF CHEMOKINE RECEPTORS

(75) Inventors: Tze-Ming Chan, Bridgewater, NJ (US); Kathleen Kox, Bridgewater, NJ (US); Wenqing Feng, Edison, NJ (US); Michael W. Miller, Scotch Plains, NJ (US); Daniel Weston, Nottingham (GB); Stuart W. McCombie, Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 175 days.

(21) Appl. No.: 11/358,520

(22) Filed: Feb. 21, 2006

(65) Prior Publication Data
US 2006/0223821 A1 Oct. 5, 2006

Related U.S. Application Data

(60) Provisional application No. 60/655,572, filed on Feb. 23, 2005.

(51) Int. Cl.
*A61K 31/497* (2006.01)
*C07D 401/00* (2006.01)

(52) U.S. Cl. .................................. 514/253.09; 544/364
(58) Field of Classification Search ............ 514/253.11; 544/31, 497
See application file for complete search history.

(56) References Cited

U.S. PATENT DOCUMENTS

| | | | |
|---|---|---|---|
| 6,387,930 B1 | 5/2002 | Baroudy et al. | |
| 6,391,865 B1 * | 5/2002 | Baroudy et al. | 514/63 |
| 6,602,885 B2 | 8/2003 | Baroudy et al. | |
| 6,689,765 B2 * | 2/2004 | Baroudy et al. | 514/63 |
| 6,720,325 B2 | 4/2004 | Miller | |
| 2007/0213346 A1 * | 9/2007 | Janssens et al. | 514/253.09 |

FOREIGN PATENT DOCUMENTS

| | | | |
|---|---|---|---|
| WO | WO 00/66558 | * | 11/2000 |
| WO | WO 2004/056770 | | 7/2004 |

OTHER PUBLICATIONS

Gray, et al., Uncoupling Coreptor Usage of Human Immunodeficiency Virus Type 1 (HIV-1) from Macrophage Tropism Reveals Biological Properties of CCR5-restricted HIV-1 Isolates from Patients with Acquired Immunodeficiency Syndrome, Virology 337, 384-398 (2005).*
West, Anthony R., Solid State Chemistry and Its Applications, Wiley, New York, 1988, 358.*
International Search Report for International Application No. PCT/US2006/006333, mailed Jun. 22, 2006—4pgs.
Antonio Mastrolorenzo, et. al., Small molecule antagonists of chemokine receptors as emerging anti-HIV agents, Expert Opin. Ther. Patents, 2001, 1245-1252, 11(8).
David Chantry, HIV entry and fusion inhibitors, Expert Opin. Emerg. Drugs, 2004, 1-7, 9(1).
Christian Watson, et. al., The CCR5 Receptor-Based Mechanism of Action of 873140, a Potent Allosteric Noncompetitive HIV Entry Inhibitor, Molecular Pharmacology, 2005, 1268-1282, 67.

* cited by examiner

*Primary Examiner*—James O Wilson
*Assistant Examiner*—Erich A Leeser
(74) *Attorney, Agent, or Firm*—Krishna G. Banerjee

(57) ABSTRACT

In its many embodiments, the present invention provides a novel class of compounds of structural formula IA or IB where $R^1$-$R^8$ are as disclosed herein

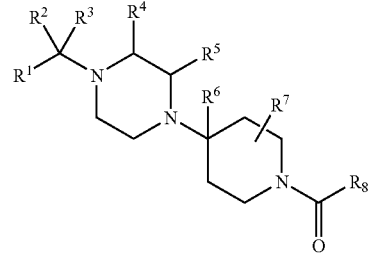

Formula IA or IB as inhibitors of the CCR5 receptors, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with CCR5 using such compounds or pharmaceutical compositions. The invention also relates to the use of a combination of a compound of this invention and one or more antiviral or other agents useful in the treatment of Human Immunodeficiency Virus (HIV). The invention further relates to the use of a compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

20 Claims, No Drawings

PIPERIDINYL PIPERAZINE DERIVATIVES USEFUL AS INHIBITORS OF CHEMOKINE RECEPTORS

This Application claims the benefit of U.S. Provisional Application Ser. No. 60/655,572 filed Feb. 23, 2005, which is incorporated herein by reference in its entirety.

FIELD OF THE INVENTION

The present invention relates to piperidinyl piperazine compounds useful as selective inhibitors of chemokine receptors, especially of the CCR5 receptors, pharmaceutical compositions containing the compounds of this invention, and methods of treatment using the inventive compounds. The invention also relates to the use of a combination of one or more compounds of this invention and one or more antiviral or other agents useful in the treatment of Human Immunodeficiency Virus (HIV). The invention further relates to the use of a compound of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

BACKGROUND OF INVENTION

The global health crisis caused by HIV, the causative agent of Acquired Immunodeficiency Syndrome (AIDS), is unquestioned. While recent advances in drug therapies have been successful in slowing the progression of AIDS, there is still a need to find a safer, more efficient, less expensive way to control the virus.

It has been reported that the CCR5 (CC Chemokine Receptor 5) gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR5 receptors have been reported to mediate cell transfer in inflammatory diseases such as arthritis, rheumatoid arthritis, atopic dermatitis, psoriasis, asthma and allergies. Inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

Piperidine derivatives, which are muscarinic antagonists useful in the treatment of cognitive disorders such as Alzheimer's disease, are disclosed in U.S. Pat. Nos. 5,883,096, 6,037,352, 5,889,006, 5,952,349, and 5,977,138.

Compounds useful as CCR5 receptor antagonists are disclosed in U.S. Pat. Nos. 6,387,930; 6,602,885 and 6,391,865, PCT Publications WO 2000/66558, WO 2000/66559, WO 02/079194, WO 03/69252, WO 03/020716, WO 04/056770, European patent publication EP1421075, and US patent publications US 2004/0092745 and US 2004/0092551 and in U.S. provisional application Ser. No. 60/516,954 filed Nov. 3, 2003.

PCT Publication WO 2002/081449 published Oct. 17, 2002 (R. Albert et al), discloses certain bipiperidinyl derivatives useful as chemokine receptor inhibitors.

A-M. Vandamme et al., *Antiviral Chemistry & Chemotherapy*, 9:187-203 (1998) disclose current clinical treatments of HIV-1 infections in man including at least triple drug combinations or so-called Highly Active Antiretroviral Therapy ("HAART"). HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and the progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

The present invention provides a novel class of compounds as antagonists of the CCR5 receptor, methods of preparing such compounds, pharmaceutical compositions containing one or more such compounds, and methods of treatment, prevention or amelioration of one or more diseases associated with the CCR5 receptor.

One aspect of the invention relates to a compound represented by the structural formula IA:

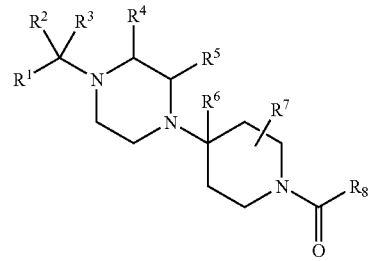

Formula IA or a pharmaceutically acceptable salt, solvate or ester thereof; wherein:

$R^1$ is selected from the group consisting of $R^9$-phenyl, $R^9$-pyridyl, $R^9$-thiophenyl, $R^9$-naphthyl, and

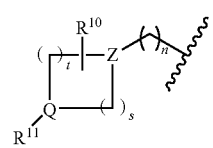

$R^2$ is selected from the group consisting of H and alkyl;

$R^3$ is selected from the group consisting of H, alkyl, alkoxyalkyl-, cycloalkyl, cycloalkylalkyl-, $R^9$-aryl, $R^9$-arylalkyl-, $R^9$-heteroaryl, and $R^9$-heteroarylalkyl-;

or $R^2$ and $R^3$ together are $=$O, $=$N(OR$^{12}$), or $=$N—N(R$^{13}$)(R$^{14}$);

$R^4$, $R^5$, $R^6$ and $R^7$ are independently selected from the group consisting of H and alkyl;

$R^8$ is selected from the group consisting of

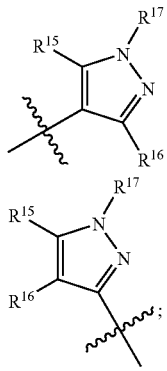
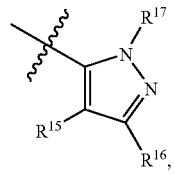 and $R^9$ is 1, 2 or 3 substituents independently selected from the group consisting of H, halogen, alkyl, alkoxy, —$CF_3$, —$OCF_3$, $CH_3C(O)$—, —CN, $CH_3S(O_2)$—, $CF_3S(O_2)$—, —$N(R^{18})(R^{19})$;

$R^{10}$ is selected from the group consisting of H and alkyl;

$R^{11}$ is selected from the group consisting of H, alkyl, fluoroalkyl-, $R^9$-arylalkyl-, $R^9$-heteroaryl-, alkyl, alkyl-$S(O_2)$—, cycloalkyl-$S(O_2)$—, fluoroalkyl-$S(O_2)$—, $R^9$-aryl-$S(O_2)$—, $R^9$-heteroaryl-$S(O_2)$—, $N(R^{18})(R^{19})$—$S(O_2)$—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

$R^{12}$ is H, alkyl, fluoroalkyl-, cycloalkylalkyl-, hydroxyalkyl-, alkyl-O-alkyl-, alkyl-O—C(O)-alkyl- or $N(R^{18})(R^{19})$—C(O)-alkyl-;

$R^{13}$ and $R^{14}$ are independently selected from the group consisting of H, alkyl and cycloalkyl, or $R^{13}$ and $R^{14}$ together are ($C_2$-$C_6$)alkylene and form a ring with the nitrogen atom to which they are shown attached;

$R^{15}$ and $R^{16}$ are independently selected from the group consisting of alkyl, halogen, —$NR^{18}R^{19}$, —OH, —CF3, —$OCH_3$, —O-acyl and —$OCF_3$;

$R^{17}$ is selected from the group consisting of $R^{20}O$—, $H_2N$— and $R^{20}R^{21}N$—;

$R^{18}$ and $R^{19}$ are independently selected from the group consisting of H and alkyl;

$R^{20}$ is selected from the group consisting of alkyl, haloalkyl cycloalkyl, heterocyclyl, aralkyl, alkylaryl, aryl, and heteroaryl;

$R^{21}$ is selected from the group consisting of H, alkyl, fluoro-alkyl-, $R^9$-arylalkyl-, $R^9$-heteroaryl-, alkyl, alkyl-$S(O_2)$—, cycloalkyl-$S(O_2)$—, fluoroalkyl-$S(O_2)$—, $R^9$-aryl-$S(O_2)$—, $R^9$-heteroaryl-$S(O_2)$—, $N(R^{18})(R^{19})$—$S(O_2)$—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

Another aspect of the invention relates to a compound in isolated and purified form, said compound represented by the structural formula IB:

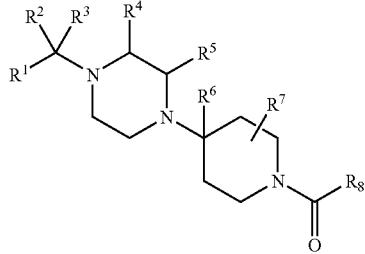

Formula IB or a pharmaceutically acceptable salt, solvate or ester thereof; wherein:

$R^1$ is selected from the group consisting of $R^9$-phenyl, $R^9$-pyridyl, $R^9$-thiophenyl, $R^9$-naphthyl, and

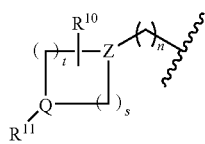

$R^2$ is selected from the group consisting of H and alkyl;

$R^3$ is selected from the group consisting of H, alkyl, alkoxyalkyl-, cycloalkyl, cycloalkylalkyl-, $R^9$-aryl, $R^9$-arylalkyl-, $R^9$-heteroaryl, and $R^9$-heteroarylalkyl-;

or $R^2$ and $R^3$ together are =O, =$NOR^{12}$, or =N—$N(R^{13})(R^{14})$;

$R^4$, $R^5$, $R^6$ and $R^7$ are independently selected from the group consisting of H and alkyl;

$R^8$ is selected from the group consisting of

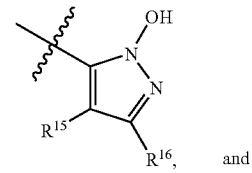 and

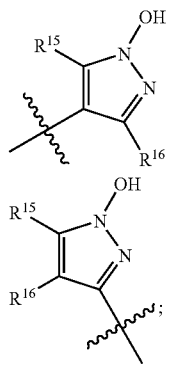

$R^9$ is 1, 2 or 3 substituents independently selected from the group consisting of H, halogen, alkyl, alkoxy, —$CF_3$, —$OCF_3$, $CH_3C(O)$—, —CN, $CH_3S(O_2)$—, $CF_3S(O_2)$—, —$N(R^{18})(R^{19})$;

$R^{10}$ is selected from the group consisting of H and alkyl;

$R^{11}$ is selected from the group consisting of H, alkyl, fluoroalkyl-, $R^9$-arylalkyl-, $R^9$-heteroaryl-, alkyl, alkyl-$S(O_2)$—, cycloalkyl-$S(O_2)$—, fluoroalkyl-$S(O_2)$—, $R^9$-aryl-$S(O_2)$—, $R^9$-heteroaryl-$S(O_2)$—, $N(R^{18})(R^{19})$—$S(O_2)$—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

$R^{12}$ is H, alkyl, fluoroalkyl-, cycloalkylalkyl-, hydroxyalkyl-, alkyl-O-alkyl-, alkyl-O—C(O)-alkyl- or $N(R^{17})(R^{18})$—C(O)-alkyl-;

$R^{13}$ and $R^{14}$ are independently selected from the group consisting of H, alkyl and cycloalkyl, or $R^{13}$ and $R^{14}$ together are $(C_2-C_6)$alkyl and form a ring with the nitrogen atom to which they are shown attached;

$R^{15}$ and $R^{16}$ are independently selected from the group consisting of alkyl, halogen, —$NR^{17}R^{18}$, —OH, —$CF_3$, —$OCH_3$, —O-acyl and —$OCF_3$;

$R^{17}$ and $R^{18}$ are independently selected from the group consisting of H and alkyl;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

The compounds of Formula IA or Formula IB can be useful as CCR5 inhibitors and in the treatment and prevention of diseases associated with CCR5 and Human Immunodeficiency Virus.

DETAILED DESCRIPTION OF THE INVENTION

In one embodiment, the present invention discloses piperidinyl piperazine compounds which are represented by structural Formula IA or IB, or a pharmaceutically acceptable salt, solvate or ester thereof, wherein the various moieties are as described above.

In another embodiment, for structural formula IA, $R^2$ is selected from the group consisting of H and $(C_1-C_6)$alkyl;

$R^3$ is selected from the group consisting of H, $(C_1-C_6)$alkyl, $(C_1-C_6)$alkoxy$(C_1-C_6)$alkyl-, $(C_3-C_{10})$cycloalkyl, $(C_3-C_{10})$cycloalky$(C_1-C_6)$lalkyl-, $R^9$-aryl, $R^9$-aryl$(C_1-C_6)$alkyl-, $R^9$-heteroaryl, and $R^9$-heteroaryl$(C_1-C_6)$alkyl-;

or $R^2$ and $R^3$ together are =O, =N($OR^{12}$), or =N—N($R^{13}$)($R^{14}$);

$R^4$, $R^5$, $R^6$ and $R^7$ are independently selected from the group consisting of H and $(C_1-C_6)$alkyl;

$R^8$ is selected from the group consisting of

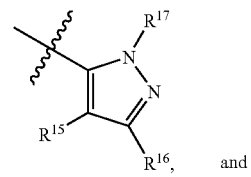

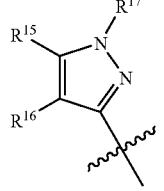

$R^9$ is 1, 2 or 3 substituents independently selected from the group consisting of H, halogen, $(C_1-C_6)$alkyl, $(C_1-C_6)$alkoxy, —$CF_3$, —$OCF_3$, $CH_3C(O)$—, —CN, $CH_3S(O_2)$—, $CF_3S(O_2)$—, —$N(R^{18})(R^{19})$;

$R^{10}$ is selected from the group consisting of H and $(C_1-C_6)$alkyl;

$R^{11}$ is selected from the group consisting of H, $(C_1-C_6)$alkyl, fluoro$(C_1-C_6)$alkyl-, $R^9$-aryl$(C_1-C_6)$alkyl-, $R^9$-heteroaryl-, $(C_1-C_6)$alkyl, $(C_1-C_6)$alkyl-$S(O_2)$—, $(C_3-C_6)$cycloalkyl-$S(O_2)$—, fluoro$(C_1-C_6)$alkyl-$S(O_2)$—, $R^9$-aryl-$S(O_2)$—, $R^9$-heteroaryl-$S(O_2)$—, $N(R^{18})(R^{19})$—$S(O_2)$—, $(C_1-C_6)$alkyl-C(O)—, $(C_3-C_6)$cycloalkyl-C(O)—, fluoro$(C_1-C_6)$alkyl-C(O)—, $R^9$-aryl-C(O)—, $(C_1-C_6)$alkyl-NH—C(O)— and $R^9$-aryl-NH—C(O)—;

$R^{12}$ is H, $(C_1-C_6)$alkyl, fluoro$(C_1-C_6)$alkyl-, $(C_3-C_{10})$cycloalkyl$(C_1-C_6)$alkyl-, hydroxy$(C_1-C_6)$alkyl-, $(C_1-C_6)$alkyl-O—$(C_2-C_6)$alkyl-, $(C_1-C_6)$alkyl-O—C(O)— $(C_1-C_6)$alkyl- or $N(R^{18})(R^{19})$—C(O)— $(C_1-C_6)$alkyl-;

$R^{13}$ and $R^{14}$ are independently selected from the group consisting of H, $(C_1-C_6)$alkyl and $(C_3-C_{10})$cycloalkyl, or $R^{13}$ and $R^{14}$ together are $(C_2-C_6)$alkyl and form a ring with the nitrogen atom to which they are shown attached;

$R^{15}$ and $R^{16}$ are independently selected from the group consisting of $(C_1-C_6)$alkyl, halogen, —$NR^{18}R^{19}$, —OH, —CF3, —$OCH_3$, —O-acyl and —$OCF_3$;

$R^{17}$ is selected from the group consisting of $R^{20}O$—, $H_2N$— and $R^{20}R^{21}N$—;

$R^{18}$ and $R^{19}$ are independently selected from the group consisting of H and $(C_1-C_6)$alkyl;

$R^{20}$ is selected from the group consisting of $(C_1-C_6)$alkyl, halo$(C_1-C_6)$alkyl, $(C_3-C_{10})$cycloalkyl, heterocyclyl, aryl$(C_1-C_6)$alkyl, $(C_1-C_6)$alkylaryl, aryl, and heteroaryl;

$R^{21}$ is selected from the group consisting of H, $(C_1-C_6)$alkyl, fluoro-$(C_1-C_6)$alkyl-, $R^9$-aryl$(C_1-C_6)$alkyl-, $R^9$-heteroaryl-, $(C_1-C_6)$alkyl, $(C_1-C_6)$alkyl-$S(O_2)$—, cyclo$(C_3-C_6)$alkyl-$S(O_2)$—, fluoro$(C_1-C_6)$alkyl-$S(O_2)$—, $R^9$-aryl-$S(O_2)$—, $R^9$-heteroaryl-$S(O_2)$—, $N(R^{18})(R^{19})$—$S(O_2)$—, $(C_1-C_6)$alkyl-C(O)—, $(C_3-C_6)$cycloalkyl-C(O)—, fluoro$(C_1-C_6)$alkyl-C(O)—, $R^9$-aryl-C(O)—, $(C_1-C_6)$alkyl-NH—C(O)— and $R^9$-aryl-NH—C(O)—;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

In another embodiment, for the compound of structural formula IB, $R^2$ is selected from the group consisting of H and $(C_1-C_6)$alkyl;

$R^3$ is selected from the group consisting of H, $(C_1-C_6)$alkyl, $(C_1-C_6)$alkoxy$(C_1-C_6)$alkyl-, $(C_3-C_{10})$cycloalkyl, $(C_3-C_{10})$cycloalky$(C_1-C_6)$lalkyl-, $R^9$-aryl, $R^9$-aryl$(C_1-C_6)$alkyl-, $R^9$-heteroaryl, and $R^9$-heteroaryl$(C_1-C_6)$alkyl-;

or $R^2$ and $R^3$ together are =O, =N($OR^{12}$), or =N—N($R^{13}$)($R^{14}$);

$R^4$, $R^5$, $R^6$ and $R^7$ are independently selected from the group consisting of H and $(C_1-C_6)$alkyl;

$R^8$ is selected from the group consisting of

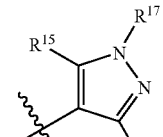 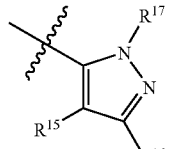 and

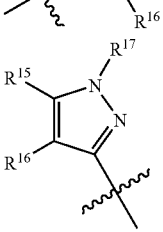

$R^9$ is 1, 2 or 3 substituents independently selected from the group consisting of H, halogen, $(C_1-C_6)$alkyl, $(C_1-C_6)$alkoxy, $-CF_3$, $-OCF_3$, $CH_3C(O)-$, $-CN$, $CH_3S(O_2)-$, $CF_3S(O_2)-$, $-N(R^{18})(R^{19})$;

$R^{10}$ is selected from the group consisting of H and $(C_1-C_6)$ alkyl;

$R^{11}$ is selected from the group consisting of H, $(C_1-C_6)$ alkyl, fluoro$(C_1-C_6)$alkyl-, $R^9$-aryl$(C_1-C_6)$alkyl-, $R^9$-heteroaryl-, $(C_1-C_6)$alkyl, $(C_1-C_6)$alkyl-$S(O_2)-$, $(C_3-C_6)$cycloalkyl-$S(O_2)-$, fluoro$(C_1-C_6)$alkyl-$S(O_2)-$, $R^9$-aryl-$S(O_2)-$, $R^9$-heteroaryl-$S(O_2)-$, $N(R^{17})(R^{18})-S(O_2)-$, $(C_1-C_6)$alkyl-$C(O)-$, $(C_3-C_6)$cycloalkyl-$C(O)-$, fluoro$(C_1-C_6)$alkyl-$C(O)-$, $R^9$-aryl-$C(O)-$, $(C_1-C_6)$alkyl-NH—$C(O)-$ and $R^9$-aryl-NH—$C(O)-$;

$R^{12}$ is H, $(C_1-C_6)$alkyl, fluoro$(C_1-C_6)$alkyl-, $(C_3-C_{10})$cycloalkyl$(C_1-C_6)$alkyl-, hydroxy$(C_1-C_6)$alkyl-, $(C_1-C_6)$alkyl-O—$(C_2-C_6)$alkyl-, $(C_1-C_6)$alkyl-O—$C(O)-$ $(C_1-C_6)$alkyl- or $N(R^{17})(R^{18})-C(O)-$ $(C_1-C_6)$alkyl-;

$R^{13}$ and $R^{14}$ are independently selected from the group consisting of H, $(C_1-C_6)$alkyl and $(C_3-C_{10})$cycloalkyl, or $R^{13}$ and $R^{14}$ together are $(C_2-C_6)$alkyl and form a ring with the nitrogen atom to which they are shown attached;

$R^{15}$ and $R^{16}$ are independently selected from the group consisting of $(C_1-C_6)$alkyl, halogen, $-NR^{17}R^{18}$, $-OH$, $-CF_3$, $-OCH_3$, $-O$-acyl and $-OCF_3$;

$R^{17}$ and $R^{18}$ are independently selected from the group consisting of H and $(C_1-C_6)$alkyl;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

In another embodiment, for the compounds of structural formula IA or IB, $R^1$ is $R^9$-phenyl.

In another embodiment for the compounds of structural formula IA or IB, $R^1$ is

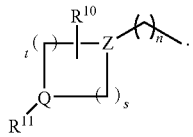

In another embodiment, for structural formula IA or IB, wherein $R^1$ is

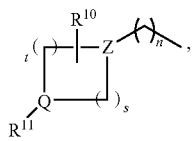

Z is CH, and Q is N.

In another embodiment, for structural formula IA or IB, $R^2$ is hydrogen and $R^3$ is selected from the group consisting of $(C_1-C_6)$alkyl, $(C_1-C_6)$alkoxy$(C_1-C_6)$alkyl-, and $R^9$-aryl.

As used herein, Structural formulae IA, IB and IC are the same except for the definition of substituent $R^8$ in said formulae.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl. Whenever applicable, the term "alkyl" also includes a divalent alkyl, i.e., an "alkylene" group, obtained by removal of a hydrogen atom from an alkyl group. Examples of alkylene groups include methylene ($-CH_2-$), ethylene ($-CH_2CH_2-$), propylene ($-C_3H_6-$) and the like including where applicable both straight chain and branched structures.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The alkynyl group may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

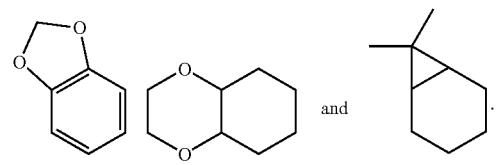

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

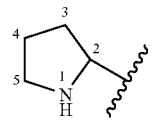

there is no —OH attached directly to carbons marked 2 and 5.

It should also be noted that tautomeric forms such as, for example, the moieties:

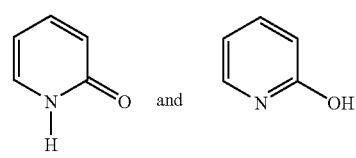

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

"Effective amount" or "therapeutically effective amount" is meant to describe an amount of compound or a composition of the present invention effective in inhibiting the diseases noted above and thus producing the desired therapeutic, ameliorative, inhibitory or preventative effect.

The compounds of Formula IA or IB can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula IA, Formula IB, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester, and prodrug of enantiomers, stereoisomers, rotamers, tautomers, positional isomers, racemates or prodrugs of the inventive compounds.

Polymorphic forms of the compounds of Formula I A and IB, and of the salts, solvates, esters and prodrugs of the compounds of Formula I, are intended to be included in the present invention.

The compounds of Formula IA and IB can be useful as CCR5 inhibitors and in the treatment and prevention of diseases associated with CCR5 and Human Immunodeficiency Virus. They can be useful for the treatment, prevention and/or amelioration of diseases such as, for example, Acquired Immune Deficiency Syndrome ("AIDS"), solid organ transplant rejection, graft v. host disease, arthritis, rheumatoid arthritis, inflammatory bowel disease, atopic dermatitis, psoriasis, asthma, allergies or multiple sclerosis. Thus, an aspect of the invention relates to a pharmaceutical composition for treatment of HIV comprising one or more compounds of formula IA or formula IB.

Yet another aspect of the invention relates to a method of treating Human Immunodeficiency Virus comprising administering to a patient in need of such treatment a therapeutically effective amount of one or more compounds of formula IA or IB. A further aspect of the invention relates to a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula IA or IB.

Still another aspect of this invention relates to a method of treating Human Immuno-deficiency Virus comprising administering to a patient in need of such treatment the one or more compounds of formula IA or IB in combination with one or more antiviral or other agents useful in the treatment. A further aspect of this invention relates to a method of treating solid organ transplant rejection, graft v. host disease, arthritis, rheumatoid arthritis, inflammatory bowel disease, atopic dermatitis, psoriasis, asthma or allergies comprising administering to a patient in need of such treatment one or more compounds of formula IA or IB in combination with one or more antiviral or other agents useful in the treatment. The CCR5 and antiviral or other agents which are components of the combination can be administered in a single dosage or administered separately. A kit comprising separate dosage forms of the actives is also contemplated.

Non-limiting examples of such combination agents include nucleoside and nucleotide reverse transcriptase inhibitors ("NRTI"s), non-nucleoside reverse transcriptase inhibitors ("NNRTI"s), protease inhibitors ("PI"s), other antiviral agents, anti-HIV therapy agents and the like.

The term "nucleoside and nucleotide reverse transcriptase inhibitors" as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR trade name from Glaxo-Wellcome Inc., Research Triangle, N.C. 27709; didanosine (ddI) available under the VIDEX trade name from Bristol-Myers Squibb Co., Princeton, N.J. 08543; zalcitabine (ddC) available under the HIVID trade name from Roche Pharmaceuticals, Nutley, N.J. 07110; stavudine (d4T) available under the ZERIT trademark from Bristol-Myers Squibb Co., Princeton, N.J. 08543; lamivudine (3TC) available under the EPIVIR trade name from Glaxo-Wellcome Research Triangle, N.C. 27709; abacavir (1592U89) disclosed in WO96/30025 and available under the ZIAGEN trademark from Glaxo-Wellcome Research Triangle, N.C. 27709; adefovir dipivoxil [bis(POM)-PMEA] available under the PREVON trade name from Gilead Sciences, Foster City, Calif. 94404; lobucavir (BMS-180194), a nucleoside reverse transcriptase inhibitor disclosed in EP-0358154 and EP-0736533 and under development by Bristol-Myers Squibb, Princeton, N.J. 08543; BCH-10652, a reverse transcriptase inhibitor (in the form of a racemic mixture of BCH-10618 and BCH-10619) under development by Biochem Pharma, Laval, Quebec H7V, 4A7, Canada; emitricitabine [(-)—FTC] licensed from Emory University under Emory Univ. U.S. Pat. No. 5,814, 639 and under development by Triangle Pharmaceuticals, Durham, N.C. 27707; beta-L-FD4 (also called beta-L-D4C and named beta-L-2',3'-dicleoxy-5-fluoro-cytidene) licensed by Yale University to Vion Pharmaceuticals, New Haven Conn. 06511; DAPD, the purine nucleoside, (-)-beta-D-2,6,-diamino-purine dioxolane disclosed in EP 0656778 and licensed by Emory University and the University of Georgia to Triangle Pharmaceuticals, Durham, N.C. 27707; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc., West Conshohocken, Pa. 19428.

The term "non-nucleoside reverse transcriptase inhibitors" as used herein means non-nucleosides that inhibit the activity of HIV-1 reverse transcriptase.

Typical suitable NNRTIs include nevirapine (BI-RG-587) available under the VIRAMUNE trade name from Boehringer Ingelheim, the manufacturer for Roxane Laboratories, Columbus, Ohio 43216; delaviradine (BHAP, U-90152) available under the RESCRIPTOR trade name from Pharmacia & Upjohn Co., Bridgewater N.J. 08807; efavirenz (DMP-266) a benzoxazin-2-one disclosed in WO94/03440 and available under the SUSTIVA trade name from DuPont Pharmaceutical Co., Wilmington, Del. 19880-0723; PNU-142721, a furopyridine-thio-pyrimide under development by Pharmacia and Upjohn, Bridgewater N.J. 08807; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019 and under clinical development by Agouron Pharmaceuticals, Inc., LaJolla Calif. 92037-1020; MKC-442 (1-(ethoxy-methyl)-5-(1-methylethyl)-6-(phenylmethyl)-(2,4(1H,3H)-pyrimidinedione) discovered by Mitsubishi Chemical Co. and under development by Triangle Pharmaceuticals, Durham, N.C. 27707; and (+)-calanolide A (NSC-675451) and B, coumarin derivatives disclosed in NIH U.S. Pat. No. 5,489,697, licensed to Med Chem Research, which is co-developing (+) calanolide A with Vita-Invest as an orally administrable product.

The term "protease inhibitor" as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN(available from Merck) as well as nonpeptide protease inhibitors e.g., VIRACEPT (available from Agouron).

Typical suitable PIs include saquinavir (Ro 31-8959) available in hard gel capsules under the INVIRASE trade name and as soft gel capsules under the FORTOVASE trade name from Roche Pharmaceuticals, Nutley, N.J. 07110-1199; ritonavir (ABT-538) available under the NORVIR trade name from Abbott Laboratories, Abbott Park, Ill. 60064; indinavir (MK-639) available under the CRIXIVAN trade name from Merck & Co., Inc., West Point, Pa. 19486-0004; nelfnavir (AG-1343) available under the VIRACEPT trade name from Agouron Pharmaceuticals, Inc., LaJolla Calif. 92037-1020; amprenavir (141W94), trade name AGENERASE, a nonpeptide protease inhibitor under development by Vertex Pharmaceuticals, Inc., Cambridge, Mass. 02139-4211 and available from Glaxo-Wellcome, Research Triangle, N.C. under an expanded access program; lasinavir (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

Other antiviral agents include hydroxyurea, ribavirin, IL-2, IL-12, pentafuside and Yissum Project No. 11607. Hydroyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) trade name from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4+ and HIV-1-RNA plasma levels should be monitored every 3-6 months. Should viral load plateau, a fourth drug, e.g., one PI or one NNRTI could be added. See the table below wherein typical therapies are further described:

Anti-HIV-1 Multi Drug Combination Therapies

A. Triple Combination Therapies
1. Two NRTIs[1]+one PI[2]
2. Two NRTIs[1]+one NNRTI[3]

B. Quadruple Combination Therapies[4]
  Two NRTIs+one PI+a second PI or one NNRTI C. Alternatives:[5]
  Two NRTI[1]
  One NRTI[5]+one PI[2]
  Two PIs[6]+one NRTI[7] or NNRTI[3]
  One PI[2]+one NRTI[7]+one NNRTI[3]
  Footnotes to Table
1. One of the following: zidovudine+lamivudine; zidovudine+didanosine; stavudine+lamivudine; stavudine+didanosine; zidovudine+alcitabine
2. Indinavir, nelfinavir, ritonavir or saquinavir soft gel capsules.
3. Nevirapine or delavirdine.
4. See A-M. Vandamne et al Antiviral Chemistry & Chemotherapy 9:187 at p. 193-197 and FIGS. 1+2.
5. Alternative regimens are for patients unable to take a recommended regimen because of compliance problems or toxicity, and for those who fail or relapse on a recommended regimen. Double nucleoside combinations may lead to HIV-resistance and clinical failure in many patients.
6. Most data obtained with saquinavir and ritonavir (each 400 mg bid).
7. Zidovudine, stavudine or didanosine.

Another embodiment of the invention provides a method of determining if a patient has been administered the compound of the formula

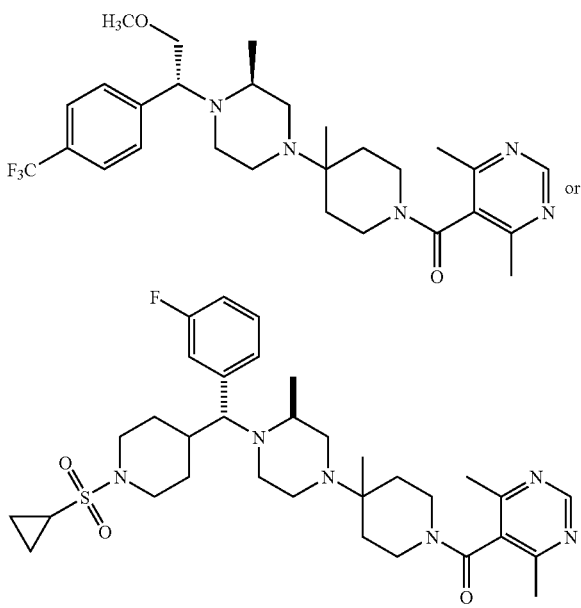

the method comprising the step of determining if a plasma, urine, bile or fecal sample obtained from the patient shows the presence of a compound of structural formula IB.

Another embodiment of the invention provides a process for preparing a compound represented by the structural formula IC:

Formula IC

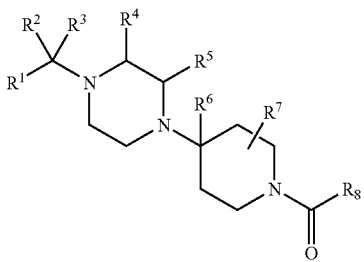

or a pharmaceutically acceptable salt, solvate or ester thereof; wherein:

$R^1$ is selected from the group consisting of $R^9$-phenyl, $R^9$-pyridyl, $R^9$-thiophenyl, $R^9$-naphthyl, and

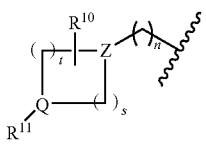

$R^2$ is selected from the group consisting of H and alkyl;

$R^3$ is selected from the group consisting of H, alkyl, alkoxyalkyl-, cycloalkyl, cycloalkylalkyl-, $R^9$-aryl, $R^9$-arylalkyl-, $R^9$-heteroaryl, and $R^9$-heteroarylalkyl-;

or $R^2$ and $R^3$ together are =O, =N(OR$^{12}$), or =N—N($R^{13}$)($R^{14}$);

$R^4$, $R^5$, $R^6$ and $R^7$ are independently selected from the group consisting of H and alkyl;

$R^8$ is selected from the group consisting of

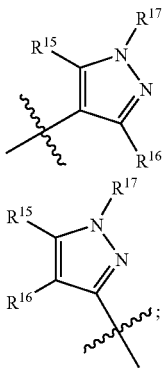 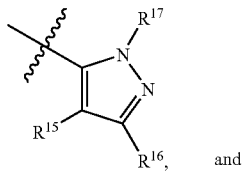 and

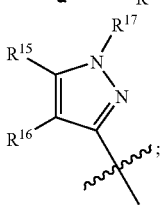 ;

$R^9$ is 1, 2 or 3 substituents independently selected from the group consisting of H, halogen, alkyl, alkoxy, —CF$_3$, —OCF$_3$, CH$_3$C(O)—, —CN, CH$_3$S(O$_2$)—, CF$_3$S(O$_2$)—, —N(R$^{18}$)(R$^{19}$);

$R^{10}$ is selected from the group consisting of H and alkyl;

$R^{11}$ is selected from the group consisting of H, alkyl, fluoroalkyl-, $R^9$-arylalkyl-, $R^9$-heteroaryl-, alkyl, alkyl-S(O$_2$)—, cycloalkyl-S(O$_2$)—, fluoroalkyl-S(O$_2$)—, $R^9$-aryl-S(O$_2$)—, $R^9$-heteroaryl-S(O$_2$)—, N(R$^{18}$)(R$^{19}$)—S(O$_2$)—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

$R^{12}$ is H, alkyl, fluoroalkyl-, cycloalkylalkyl-, hydroxyalkyl-, alkyl-O-alkyl-, alkyl-O—C(O)-alkyl- or N(R$^{18}$)(R$^{19}$)—C(O)-alkyl-;

$R^{13}$ and $R^{14}$ are independently selected from the group consisting of H, alkyl and cycloalkyl, or $R^{13}$ and $R^{14}$ together are (C$_2$-C$_6$)alkylene and form a ring with the nitrogen atom to which they are shown attached;

$R^{15}$ and $R^{16}$ are independently selected from the group consisting of alkyl, halogen, —NR$^{18}$R$^{19}$, —OH, —CF3, —OCH$_3$, —O-acyl and —OCF$_3$;

$R^{17}$ is selected from the group consisting of R$^{20}$O—, and R$^{20}$R$^{21}$N—;

$R^{18}$ and $R^{19}$ are independently selected from the group consisting of H and alkyl;

$R^{20}$ is selected from the group consisting of H, alkyl, haloalkyl cycloalkyl, heterocyclyl, aralkyl, alkylaryl, aryl, and heteroaryl;

$R^{21}$ is selected from the group consisting of H, alkyl, fluoro-alkyl-, $R^9$-arylalkyl-, $R^9$-heteroaryl-, alkyl, alkyl-S(O$_2$)—, cycloalkyl-S(O$_2$)—, fluoroalkyl-S(O$_2$)—, $R^9$-aryl-S(O$_2$)—, $R^9$-heteroaryl-S(O$_2$)—, N(R$^{18}$)(R$^{19}$)—S(O$_2$)—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH;

comprising reacting an amine of the formula

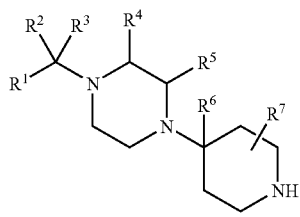

with a carboxylic acid of formula R$^8$COOH or an acid chloride of formula R$^8$C(O)Cl; wherein R$^1$-R$^8$ are as set forth for Formula I.

In one embodiment of the above-mentioned process, $R^2$ is selected from the group consisting of H and (C$_1$-C$_6$)alkyl;

$R^3$ is selected from the group consisting of H, (C$_1$-C$_6$)alkyl, (C$_1$-C$_6$)alkoxy(C$_1$-C$_6$)alkyl-, (C$_3$-C$_{10}$)cycloalkyl, (C$_3$-C$_{10}$)cycloalky(C$_1$-C$_6$)lalkyl-, R$^9$-aryl, R$^9$-aryl(C$_1$-C$_6$)alkyl-, R$^9$-heteroaryl, and R$^9$-heteroaryl(C$_1$-C$_6$)alkyl-;

or $R^2$ and $R^3$ together are =O, =N(OR$^{12}$), or =N—N(R$^{13}$)(R$^{14}$);

$R^4$, $R^5$, $R^6$ and $R^7$ are independently selected from the group consisting of H and (C$_1$-C$_6$)alkyl;

$R^8$ is selected from the group consisting of

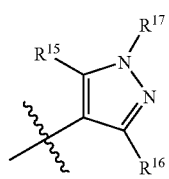 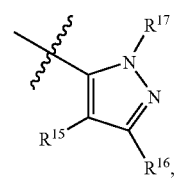 and

-continued

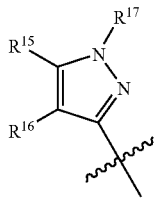

R[9] is 1, 2 or 3 substituents independently selected from the group consisting of H, halogen, ($C_1$-$C_6$)alkyl, ($C_1$-$C_6$)alkoxy, —$CF_3$, —$OCF_3$, $CH_3C(O)$—, —CN, $CH_3S(O_2)$—, $CF_3S(O_2)$—, —N(R[18])(R[19]);

R[10] is selected from the group consisting of H and ($C_1$-$C_6$)alkyl;

R[11] is selected from the group consisting of H, ($C_1$-$C_6$)alkyl, fluoro($C_1$-$C_6$)alkyl-, R[9]-aryl($C_1$-$C_6$)alkyl-, R[9]-heteroaryl-, ($C_1$-$C_6$)alkyl, ($C_1$-$C_6$)alkyl-$S(O_2)$—, ($C_3$-$C_6$)cycloalkyl-$S(O_2)$—, fluoro($C_1$-$C_6$)alkyl-$S(O_2)$—, R[9]-aryl-$S(O_2)$—, R[9]-heteroaryl-$S(O_2)$—, N(R[18])(R[19])—$S(O_2)$—, ($C_1$-$C_6$)alkyl-C(O)—, ($C_3$-$C_6$)cycloalkyl-C(O)—, fluoro($C_1$-$C_6$)alkyl-C(O)—, R[9]-aryl-C(O)—, ($C_1$-$C_6$)alkyl-NH—C(O)— and R[9]-aryl-NH—C(O)—;

R[12] is H, ($C_1$-$C_6$)alkyl, fluoro($C_1$-$C_6$)alkyl-, ($C_3$-$C_{10}$)cycloalkyl($C_1$-$C_6$)alkyl-, hydroxy($C_1$-$C_6$)alkyl-, ($C_1$-$C_6$)alkyl-O—($C_2$-$C_6$)alkyl-, ($C_1$-$C_6$)alkyl-O—C(O)— ($C_1$-$C_6$)alkyl- or N(R[18])(R[19])—C(O)— ($C_1$-$C_6$)alkyl-;

R[13] and R[14] are independently selected from the group consisting of H, ($C_1$-$C_6$)alkyl and ($C_3$-$C_{10}$)cycloalkyl, or R[13] and R[14] together are ($C_2$-$C_6$)alkyl and form a ring with the nitrogen atom to which they are shown attached;

R[15] and R[16] are independently selected from the group consisting of ($C_1$-$C_6$)alkyl, halogen, —NR[18]R[19], —OH, —CF3, —$OCH_3$, —O-acyl and —$OCF_3$;

R[17] is selected from the group consisting of R[20]O and R[20]R[21]N—;

R[18] and R[19] are independently selected from the group consisting of H and ($C_1$-$C_6$)alkyl;

R[20] is selected from the group consisting of H, ($C_1$-$C_6$)alkyl, halo($C_1$-$C_6$)alkyl, ($C_3$-$C_{10}$)cycloalkyl, heterocyclyl, aryl($C_1$-$C_6$)alkyl, ($C_1$-$C_6$)alkylaryl, aryl, and heteroaryl;

R[21] is selected from the group consisting of H, ($C_1$-$C_6$)alkyl, fluoro-($C_1$-$C_6$)alkyl-, R[9]-aryl($C_1$-$C_6$)alkyl-, R[9]-heteroaryl-, ($C_1$-$C_6$)alkyl, ($C_1$-$C_6$)alkyl-$S(O_2)$—, cyclo($C_3$-$C_6$)alkyl-$S(O_2)$—, fluoro($C_1$-$C_6$)alkyl-$S(O_2)$—, R[9]-aryl-$S(O_2)$—, R[9]-heteroaryl-$S(O_2)$—, N(R[18])(R[19])—$S(O_2)$—, ($C_1$-$C_6$)alkyl-C(O)—, ($C_3$-$C_6$)cycloalkyl-C(O)—, fluoro($C_1$-$C_6$)alkyl-C(O)—, R[9]-aryl-C(O)—, ($C_1$-$C_6$)alkyl-NH—C(O)— and R[9]-aryl-NH—C(O)—;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

In another embodiment of the above-mentioned process, the reaction of the amine with the carboxylic acid or acid chloride is conducted in the presence of one or more amidation coupling agents, such as 1-hydroxybenzotriazole (HOBT) and 1-(3-dimethylaminopropyl)-3-ethyl carbodiimide hydrochloride (DEC).

Another embodiment of the invention provides the following compounds in Table 1. Table 1 also provides the mass spectral data (HRMS) for the compounds.

TABLE 1

| Structure | HRMS |
|---|---|
| 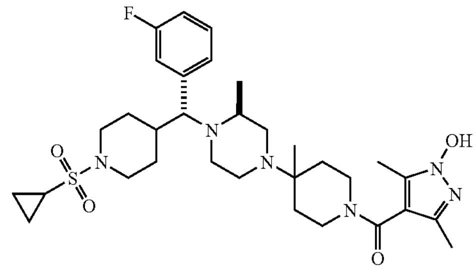 | 631.3433 |
| 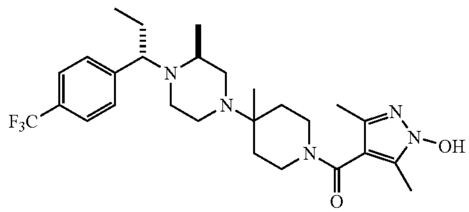 | 522.3068 |
| 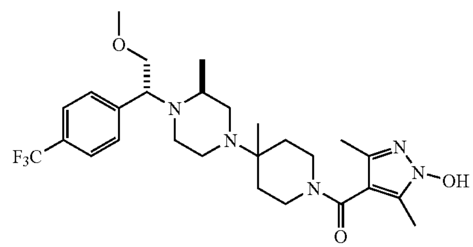 | 538.3000 |
| 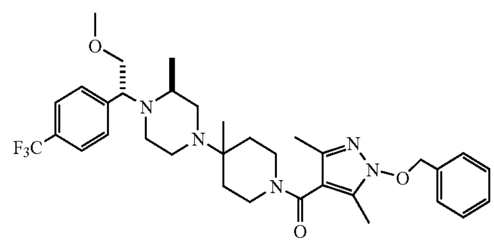 | 624.3464 |

Table 2 below additionally provides the activity data ($IC_{50}$ in nanomolar, nM) for the compounds listed in Table 1, as determined by the Luciferase Replication assay detailed in a later section of this specification.

TABLE 2

| Structure | HIV Replication $IC_{50}$ luciferase (nM, Yu-2) |
|---|---|
| 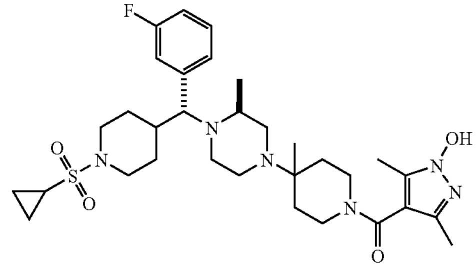 | 43 |

TABLE 2-continued

| Structure | HIV Replication IC$_{50}$ luciferase (nM, Yu-2) |
|---|---|
| 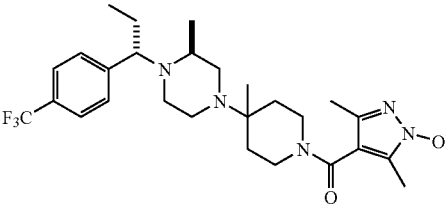 | >100 |
| 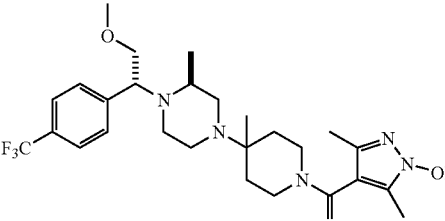 | 8 |
| 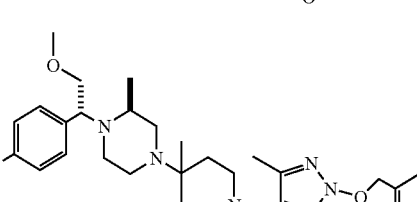 | 0.4 |

The compounds of the present invention, also referred to herein as the inventive compounds, are particularly useful as a CCR5 antagonist.

Compounds of the invention can be made by procedures known in the art, or by the methods described in the examples below. The following preparative schemes and examples should not be construed to limit the scope of the disclosure. Alternative mechanistic pathways and analogous structures within the scope of the invention may be apparent to those skilled in the art.

The following solvents and reagents may be referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine (Et$_3$N); diethyl ether (Et$_2$O); tert-butoxy-carbonyl (BOC); 1,8-diazabicyclo[5.4.0] undec-7-ene (DBU); dimethyl-sulfoxide (DMSO); p-toluene sulfonic acid (p-TSA); potassium bis(trimethylsilyl)-amide (KHMDA); 4-dimethylaminopryidine (DMAP); N,N,N-diisopropylethylamine (DIPEA); Alloc: allyloxycarbamate; MeCN: acetonitrile; and 1-(3-dimethyl-aminopropyl)-3-ethyl carbodiimide hydrochloride (EDCI, DEC or EDC). RT is room temperature.

Compounds represented by the following invention can be prepared by standard coupling conditions of an amine and carboxylic acid (R$^8$CO$_2$H) (or acid chloride, R$^8$C(O)Cl) (Scheme 1). Representative examples are shown below.

Scheme 1

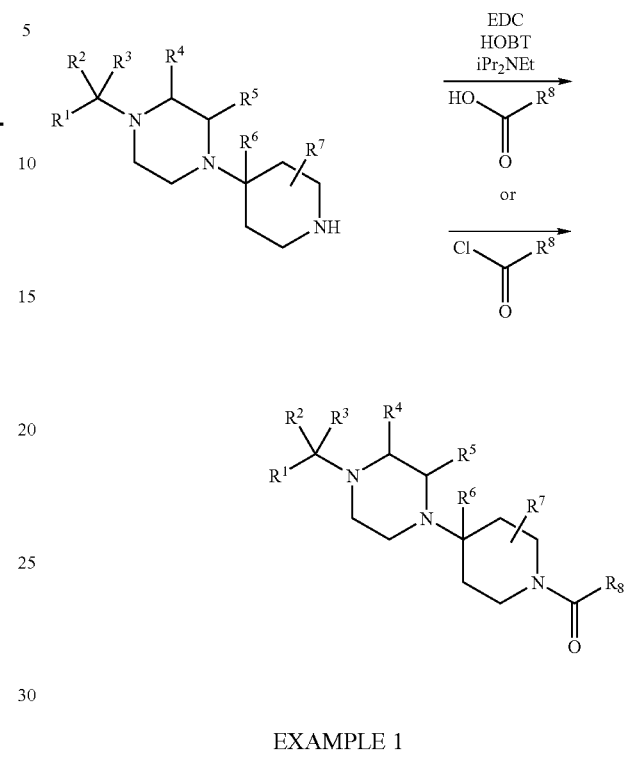

EXAMPLE 1

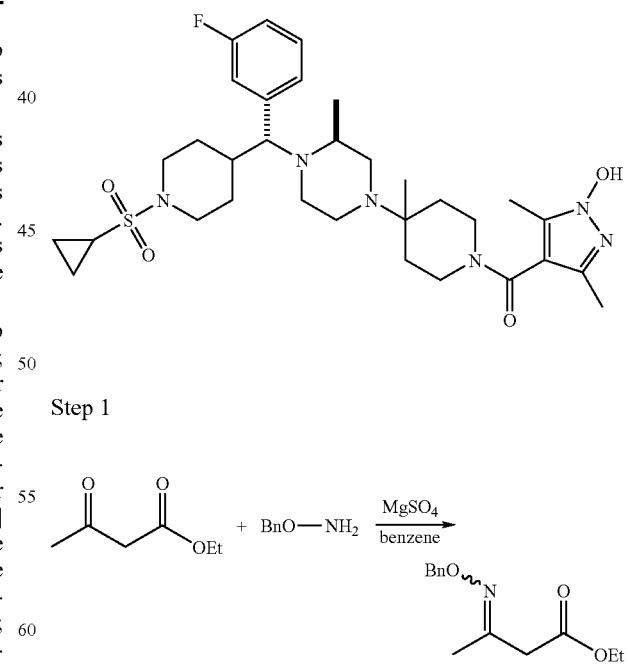

Step 1

Ethyl acetoacetate (7.5 g, 58 mmol) and O-Benzyl hydroxylamine (7.1 g, 58 mmol), and MgSO$_4$ (5 g) were taken up in benzene and stirred at 25° C. for 24 hours. Filtration and concentration gave the oxime.

Step 2

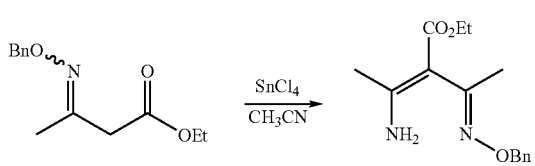

The oxime (1.0 g, 4.25 mmol) was taken up in CH₃CN (8 mL) and cooled to 0° C. SnCl₄ (4.3 ml, 1.0 M in CH2Cl2) was added dropwise to the solution at 0° C. The solution was stirred at 0° C. for one hour. The solution was quenched with saturated Na₂CO₃ (aq.). The mixture was extracted with EtOAc. The combined organic layers were washed with brine and dried (MgSO4). Filtration and concentration gave a colorless oil. Purification via flash chromatography (3/1 hexanes/EtOAc, SiO₂) gave 415 mg (35%) of the enamide as a colorless oil.

Step 3

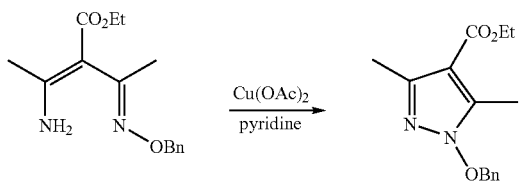

The enamide (415 mg, 1.5 mmol) and Cu(OAc)₂ (400 mg) were taken up in pyridine. The mixture was heated at 100° C. for 4 hours. The solution was cooled and concentrated. The residue was partitioned between EtOAc and 10% NH₄OH$_{(aq.)}$. The aqueous layer was extracted with EtOAc. The combined organic layers were washed with brine and dried (MgSO₄). Filtration and concentration gave a brown oil. Purification via flash chromatography (9/1 hexanes/EtOAc, SIO₂) gave 330 mg (80%) of the pyrazole as a colorless oil.

Step 4

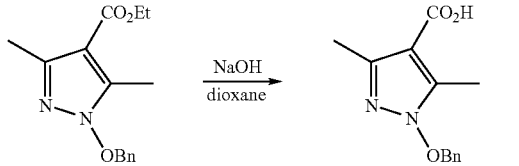

The ester (545 mg, 1.99 mmol) and 1 N NaOH$_{(aq.)}$ was taken up in dioxane/EtOH. The solution was heated at 75° C. for 24 hours. The solution was concentrated. The solution was acidified with 1 M HCl$_{(aq.)}$ (pH=2-3). The fromed white precipitate was collected and dried under high vac. The acid was obtained as a white powder (314 mg, 64%). 1H NMR (CDCl3, 400 mHz) δ2.07 (s, 3H), 2.46 (s, 3H), 5.26 (s, 2H), 7.25-7.37 (m, 5H). HRMS calc'd for $C_{13}H_{15}O_3N(MH^+)$ 247.1083; Found: 247.1089.

Step 5

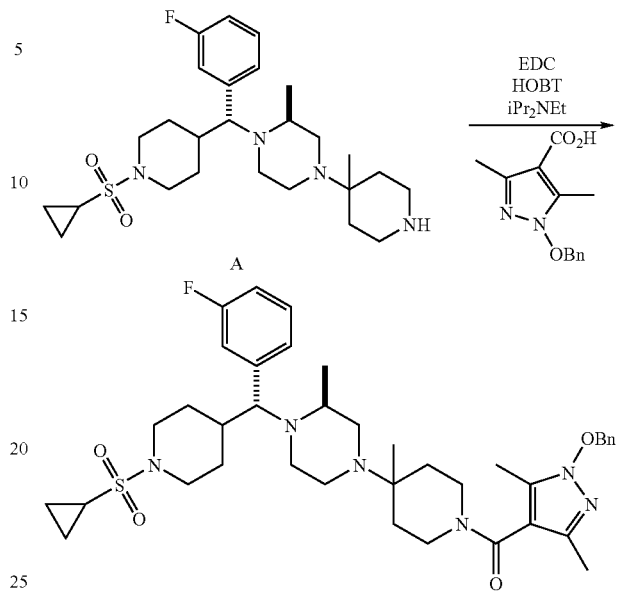

The piperidine A (see below for synthesis of A; 122 mg, 0.24 mmol), EDC (56 mg, 0.29 mmol), HOBT (40 mg, 0.29 mmol), iPr2NEt (93 mg, 0.73 mmol), and the acid (61 mg, 0.24 mmol) were taken up in CH3CN. The solution was stirred at 25° C. for 18 hours. The solution was concentrated. The residue was partitioned between EtOAc and 1 N NaOH (aq.). The aqueous layer was extracted with EtOAc. The combined EtOAc layers were washed with brine and dried (MgSO4). Filtration and concentration gave a yellow oil. Purification via preparative thin-layer chromatography 15/1 CH₂Cl₂/methanol, SiO₂ gave the amide as a colorless oil (166 mg, 95%). Low-res MS (MH⁺) 721.

Step 6

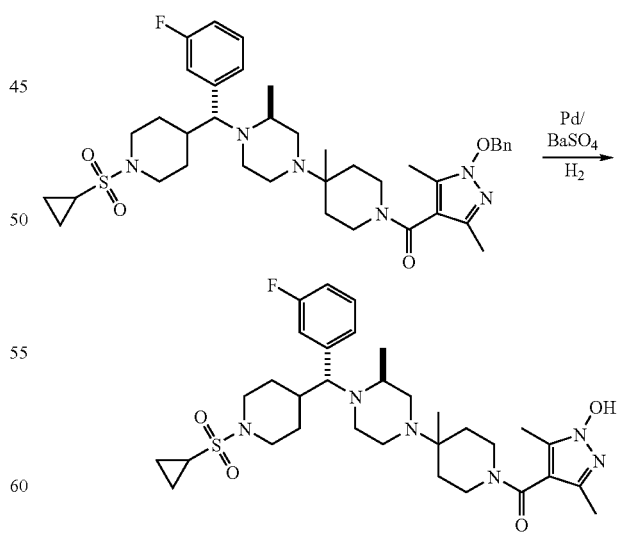

Example 1

The O-benzyl ether (135 mg, 0.19 mmol) and Pd/BaSO₄ (40 mg) were taken up in MeOH. The mixture was placed into a Parr apparatus and charged with 10 psi H₂. The mixture was shaken at 25° C. for 30 minutes. Filtration gave a yellow oil. Purification via preparative thin-layer chromatography (15/1 CH$_2$Cl$_2$/methanol, SiO$_2$) gave 79 mg (67%) of Example 1 (first compound in Table 1) as a colorless oil. m.p. (2 HCl): 214-215° C., HRMS calc'd for C$_{32}$H$_{48}$O$_4$N$_6$FS (MH$^+$): 631.3442; Found: 631.3433.

Synthesis of Piperidine A

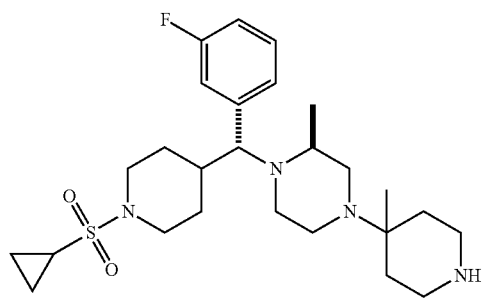

Step 1

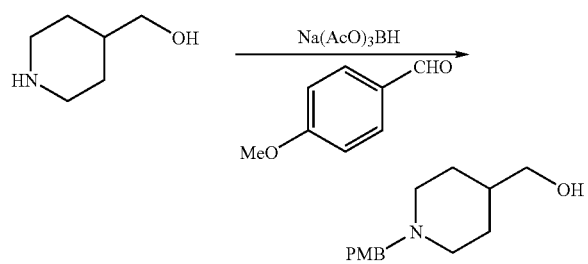

4-Piperidine-methanol (10 g), p-anisaldehyde (13 mL), and Na(AcO)$_3$BH (22 g) were taken up in CH$_2$Cl$_2$ (250 mL) and stirred at 25° C. (19 h). The solution was diluted with CH$_2$Cl$_2$ and washed with 1 N NaOH (aq.). The aqueous layer was extracted with CH$_2$Cl$_2$. The combined organic layers were dried (Na$_2$SO$_4$), filtered, and concentrated which yielded a yellow oil. The residue was taken up in Et$_2$O and washed with 1 M HCl$_{(aq.)}$. The aqueous acidic layer was extracted with Et$_2$O. The acidic layer was cooled to 0° C. and made basic via addition of NaOH pellets (pH=10-12). The mixture was extracted with CH$_2$Cl$_2$. The combined organic layers were dried (Na$_2$SO$_4$), filtered and concentrated which furnished the alcohol (18.4 g, 90%) as a thick oil.

Step 2

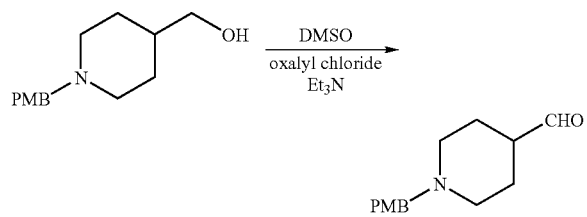

DMSO (7.2 mL) was taken up in CH$_2$Cl$_2$ (200 mL), and the resulting solution was cooled to −40° C. (CO$_2$/CH$_3$CN). Oxalyl chloride (8.9 mL) in CH$_2$Cl$_2$ (15 mL) was added dropwise to the solution at −40° C. (mechanical stirrer). After the addition, the solution was stirred at −40° C. for 30 minutes. The alcohol (18.4 g) in CH$_2$Cl$_2$ (40 mL) was added to the solution at −40° C. After the addition, the resulting solution was stirred at −40° C. for 30 minutes. Triethylamine (33 mL) was added to the solution at −40° C. at which time a precipitate formed. The mixture was stirred at −40° C. for 15 minutes and then at 25° C. for 45 minutes. The solution was diluted with CH$_2$Cl$_2$ and washed with 1 N NaOH$_{(aq.)}$. The aqueous layer was extracted with CH$_2$Cl$_2$. The combined organic layers were dried (Na$_2$SO$_4$), filtered, and concentrated which furnished the aldehyde as a yellow oil (17.7 g, 97%).

Step 3

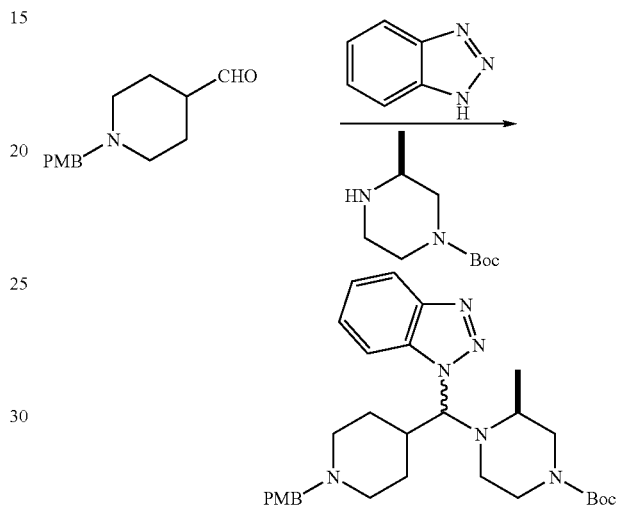

The aldehyde (11.3 g), (S)—N-Boc-methyl piperazine (9.7 g), and benzotriazole (5.7 g) were taken up in benzene (350 mL) and heated with azeotropic removal of H$_2$O (Dean-Stark trap) for 4.75 h. The solution was cooled and concentrated. The benzotriazole adduct was used as is in the next step.

Step 4

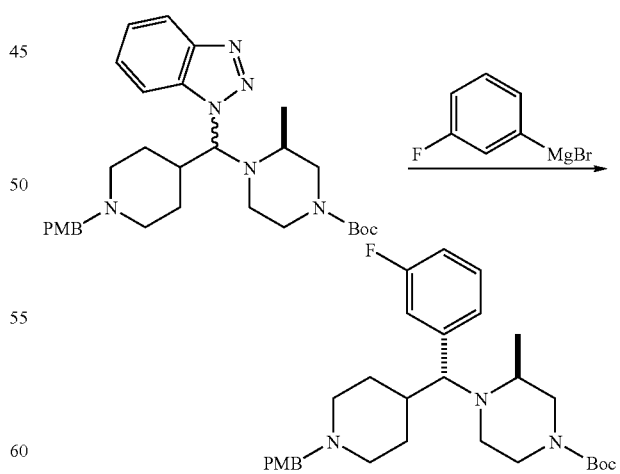

The crude benzotriazole adduct from the previous step (48 mmol) was taken up in dry THF (200 mL). The solution was cooled to 0° C. 3-Fluorophenyl magnesium bromide (290 mL of a 0.5 M solution in THF) was added to the solution at 0° C. The resulting brown, heterogenous solution was warmed to 25° C. and stirred at that temperature for 5 h. The solution was slowly quenched with 25 wt % sodium citrate, and the mixture was concentrated on the rotovap. The residue was partitioned between EtOAc and 25 wt % sodium citrate. The aqueous layer was extracted with EtOAc. The combined organic layers were washed with brine and dried (Na$_2$SO$_4$). Filtration and concentration gave a yellow oil. Purification via flash chromatography twice (1$^{st}$ time: 2/1 hexanes/acetone, 2$^{nd}$ time: 4/1 hexanes/acetone) furnished 17.8 grams (72%) of the desired piperazine as a colorless oil.

Step 5

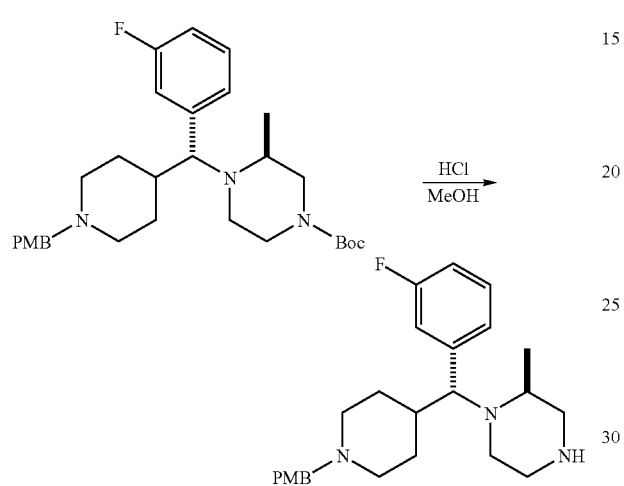

The Boc-piperazine (750 mg) and 3 ml of 4.0 M HCl in dioxane were taken up in MeOH and stirred at 25° C. (16 h). The solution was concentrated. The residue was partitioned between CH$_2$Cl$_2$ and 1 N NaOH$_{(aq.)}$. The aqueous layer was extracted with CH$_2$Cl$_2$. The combined organic layers were dried (MgSO$_4$). Filtration and concentration gave 582 mg (97%) of the piperazine as a yellow foam.

Step 6

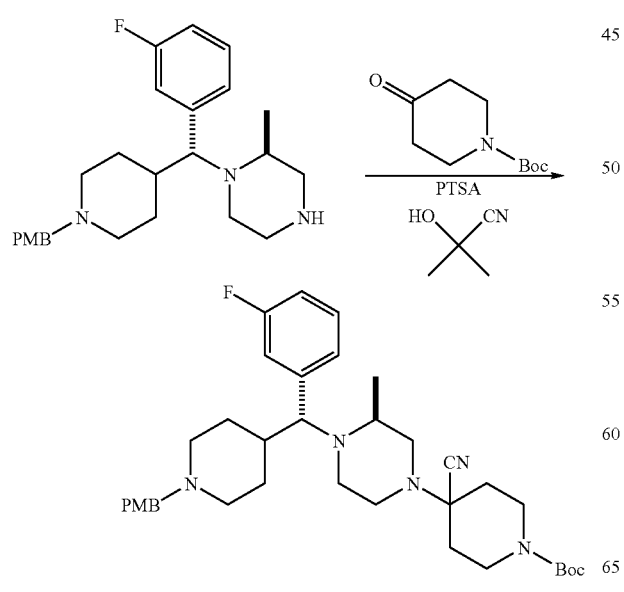

The piperazine (582 mg), N-Boc-4-piperidone (281 mg) and p-toluene sulfonic acid (3 mg) were taken up in toluene and heated at reflux with azeotropic removal of H$_2$O (Dean Stark, oil bath temp=150° C.) for 2.5 h. The solution was cooled and acetone cyanohydrin (0.2 mL) was added. The solution was heated at reflux for an additional 3 h. The solution was cooled. The cyano-amine in toluene was used as in the next step.

Step 7

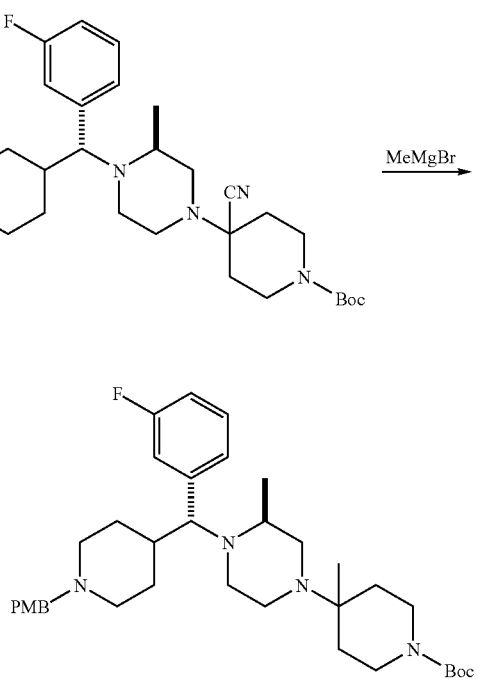

The toluene solution of the cyano-amine from above (1.4 mmol) was diluted with THF, and MeMgBr (2.4 mL of a 3.0 M solution in Et$_2$O) was added to the solution. The resulting solution was stirred at 25° C. for 18 h. The mixture was quenched with 25 wt % sodium citrate. The mixture was extracted with EtOAc. The combined organic layers were washed with brine and dried (MgSO$_4$). Filtration and concentration gave 887 mg of the methylated piperidine (100% based on the starting piperazine in Step 6).

Step 8

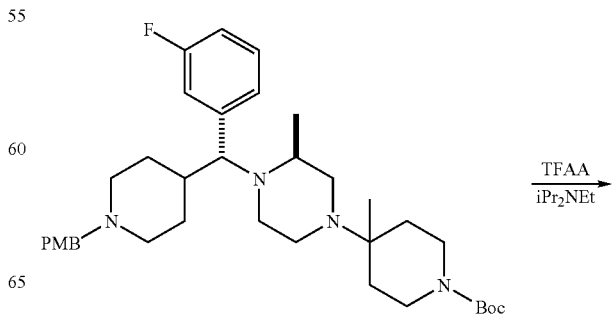

-continued

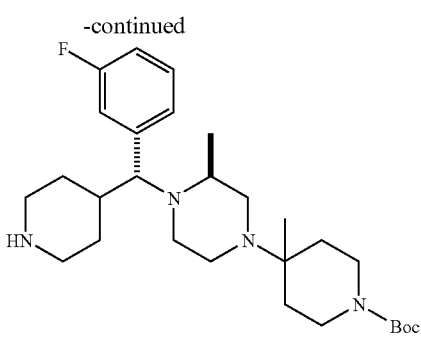

The PMB protected piperidine (887 mg) and iPr$_2$NEt (0.5 mL) were taken up in CH$_2$Cl$_2$. Trifluoroacetic anhydride (0.3 mL) was added, and the solution was stirred at 25° C. for 1 h. The solution was concentrated, and the residue was taken up in MeOH/1 N NaOH$_{(aq.)}$. The solution was heated at 75° C. for 3 h. The solution was cooled and concentrated. The residue was partitioned between CH$_2$Cl$_2$ and 1 N NaOH$_{(aq.)}$. The aqueous layer was extracted with CH$_2$Cl$_2$. The combined organic layers were dried (MgSO$_4$), filtered, and concentrated which gave the piperidine as a yellow oil. This material was used directly in the next step.

Step 9

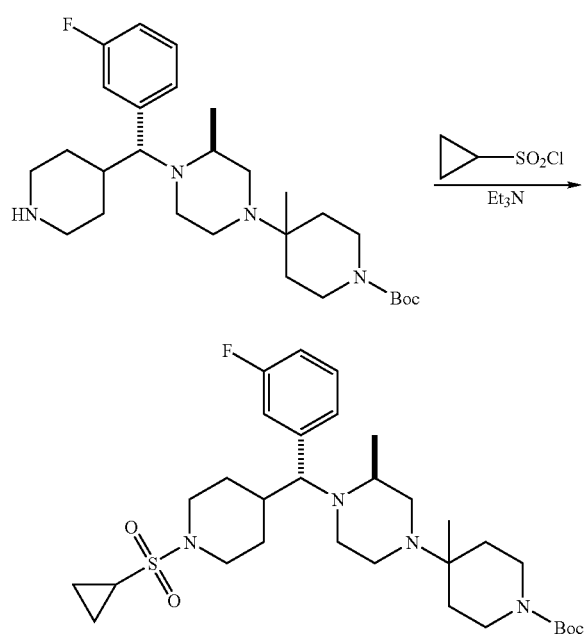

The piperidine from Step 8 (1.46 mmol) and Et$_3$N (0.45 mL) were taken up in CH$_2$Cl$_2$ and cooled to 0° C. Cyclopropylsulfonyl chloride (230 mg) was added, and the resulting solution was stirred at 25° C. (2.5 h). The solution was diluted with CH$_2$Cl$_2$ and washed with 1 N NaOH$_{(aq.)}$. The aqueous layer was extracted with CH$_2$Cl$_2$. The combined organic layers were dried (MgSO$_4$), filtered, and concentrated. The residue was purified via flash chromatography (3/1 hexanes/acetone, SiO$_2$) which gave 693 mg (80% from cyano-amine from Step 6) as a yellow oil.

Step 10

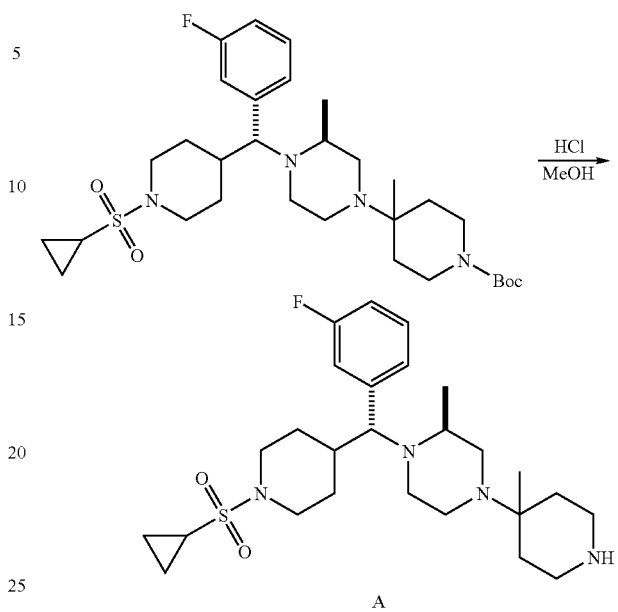

The Boc piperidine (693 mg) was taken up in MeOH. 4.0 M HCl in dioxane was added (2.5 mL), and the resulting solution was stirred at 25° C. (18 h). The solution was concentrated. The residue was partitioned between 1 M HCl$_{(aq.)}$ and Et$_2$O. The aqueous layer was extracted with Et$_2$O. The aqueous layer was cooled and basified with NaOH pellets (pH=10-12). The mixture was extracted with CH$_2$Cl$_2$. The combined CH$_2$Cl$_2$ layers were dried (MgSO$_4$), filtered, and concentrated which gave 419 mg (62%) of the Piperidine A as a yellow foam.

The remaining compounds of Table 1 were prepared using a similar procedure and appropriate reagents.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. An example of this includes, but is not limited to, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compound of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of the invention may also be administered orally, intravenously, intranasally or subcutaneously.

Preferably the compound is administered orally.

Preferably, the pharmaceutical preparation is in a unit dosage form. In such form, the preparation is subdivided into suitably sized unit doses containing a therapeutically effective amount of the compound of formula IA or IB.

The quantity of active compound in a unit dose of preparation may be varied or adjusted from about 10 mg to about 500 mg, preferably from about 25 mg to about 300 mg, more preferably from about 50 mg to about 250 mg, and most preferably from about 55 mg to about 200 mg, according to the particular application.

The actual dosage of the inventive compound employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimens of the NRTIs, NNRTIs, PIs and other agents used in combination with the compounds of this invention will be determined by the attending clinician in view of the approved doses and dosage regimens in the package inserts or as set forth in the protocols, taking into consideration the age, sex and condition of the patient and the severity of the condition treated.

In a preferred embodiment, the compound of the present invention can be used to treat Human Immunodeficiency Virus by administering to a patient in need of such treatment a therapeutically effective amount of one or more compounds of formula IA or IB, preferably in combination with one or more pharmaceutically acceptable carriers. One or more, preferably one to four, antiviral agents useful in anti-HIV-1 therapy can be used in combination with the compound of the present invention. The antiviral agent or agents can be combined with one or more compounds of the present invention in a single dosage form. The one or more compounds of the present invention and the antiviral agent or agents may be administered in any order such as, for example, sequentially, concurrently, simultaneously and the like. The amounts of the various actives in such combination therapy may be different amounts (dosage amounts) or same amounts (dosage amounts). The various actives could also be present in fixed amounts in the same dosage form, e.g., 10 mg of a compound of claim 1 and 10 mg of an anti-viral agent present in a single tablet. An illustrative such "single tablet" would be, for example, the anti-cholesterol medication VYTORIN® (available from Merck Schering-Plough Pharmaceuticals, Kenilworth, N.J.).

The antiviral agents contemplated for use in combination with the compound of the present invention comprise nucleoside and nucleotide reverse transcriptase inhibitors, non-nucleoside reverse transcriptase inhibitors, protease inhibitors and other antiviral drugs listed below not falling within these classifications. Specific examples of antiviral agents include, but are not limited to, zidovudine, lamivudine, zalcitabine, didanosine, stavudine, abacavir, adefovir dipivoxil, lobucavir, BCH-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No. 11607 and AG-1549. In particular, the combinations known as HAART are contemplated for use in combination with the compound of this invention.

For combination treatment with more than one active agent, where the active agents are in separate dosage formulations, the active agents may be administered separately or in conjunction. In addition, the administration of one element may be prior to, concurrent to, or subsequent to the administration of the other agent.

Another aspect of the invention provides a method of treating solid organ transplant rejection, graft v. host disease, arthritis, rheumatoid arthritis, inflammatory bowel disease, atopic dermatitis, psoriasis, asthma, allergies or multiple sclerosis comprising administering to a patient in need of such treatment a therapeutically effective amount of one or more compounds of formula IA or IB, preferably in combination with one or more pharmaceutically acceptable carriers. In another embodiment, the method for treating solid organ transplant rejection, graft v. host disease, rheumatoid arthritis, inflammatory bowel disease or multiple sclerosis further comprises administering one or more other agents useful in the treatment of said diseases in combination with one or more compounds of formula IA or IB.

Agents known in the treatment of rheumatoid arthritis, transplant and graft v. host disease, inflammatory bowel disease and multiple sclerosis which can be administered in combination with the compound of the present invention are as follows:

Solid organ transplant rejection and graft v. host disease: immune suppressants such as cyclosporine and Interleukin-10 (IL-10), tacrolimus, antilymphocyte globulin, OKT-3 antibody, and steroids;

Inflammatory bowel disease: IL-10 (see U.S. Pat. No. 5,368,854), steroids and azulfidine;

Rheumatoid arthritis: methotrexate, azathioprine, cyclophosphamide, steroids and mycophenolate mofetil;

Multiple sclerosis: interferon-beta, interferon-alpha, and steroids.

Another aspect of the invention relates to a kit comprising in separate containers in a single package pharmaceutical composition for use in combination to treat Human Immunodeficiency Virus. In one container, a pharmaceutical composition comprises one or more compounds of formula IA or IB in one or more pharmaceutically acceptable carriers, and in separate containers, one or more pharmaceutical compositions comprising an effective amount of one or more antiviral agents or other agents useful in the treatment of Human Immunodeficiency Virus in one or more pharmaceutically acceptable carriers.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor-1 Monitor 1.5 (available from Roche Diagnostics) or of Nuclisens HIV-1 QT-1.

Assays useful for determining the CCR5 antagonistic activity as well as the HIV replication inhibitory activity are described in detail in patent application, Serial No. IN01481 K. The following assays were used to determine the CCR5 antagonistic activity and the HIV replication inhibitory activity of the compounds of the invention.

Chemotaxis Assay: The chemotaxis assay is a functional assay which characterizes the agonist vs. antagonist properties of the test compounds. The assay measures the ability of a non-adherent murine cell line expressing human CCR5 (BaF-550) to migrate across a membrane in response to either test compounds or natural ligands (i.e., RANTES, MIP-1β). Cells migrate across the permeable membrane towards compounds with agonist activity. Compounds that are antagonists not only fail to induce chemotaxis, but are also capable of inhibiting cell migration in response to known CCR5 ligands. The activity of the inventive compounds was also measured by the Chemitaxis assay.

Chemotaxis Assay procedure: Ba/F3-hCCR5 clone 550 (a.k.a. B550) cells were cultured in RPMI-1640 supplemented with 10% fetal bovine serum (FBS), 1×Pen-Strep, 1×Glutamax, 1×HEPES, 1×2-mercaptoethanol, and mIL-3 at 1 μg/L. All tissue culture reagents were obtained from Invitrogen (Carlsbad, Calif.), unless otherwise specified. FBS was obtained from Gemini Bio-Products, Woodland, Calif. Mouse IL-3 was obtained from R and D Systems, Minneapolis, Minn.

Human MIP-1β(hMIP-1β) was purchased from R and D Systems and was used at a final concentration of 1 nM in the assay. The compounds were reconstituted in DMSO and diluted in the chemotaxis assay medium, from 0.1 nM to 1000 nM (final concentrations).

For assay, the cells were washed twice in plain RPMI 1640 medium, and then resuspended at the appropriate concentration in the assay medium. The assay medium consisted 10% Ba/F3 media in RPMI 1640. The final density of cells for the assay was approximately cells at 2.5×10⁶ per ml. Chemotaxis was performed using the 96-well ChemoTx system® with 5 micron filter pore size (NeuroProbe, Inc., Gaithersburg, Md., Cat. #: 101-5).

The compounds were used in an antagonist chemotaxis setup according to the manufacturer's instructions. Briefly, each compound was mixed with hMIP-1β and approximately 29 μl of the mixture was placed in the bottom well of the 96-well ChemoTx system. The filter screen was placed on top and 25 μl of cells mixed with the appropriate concentration of compound was placed on the filter. The assembled plates were incubated for 2 hours at 37° C. in a humidified chamber. After incubation the cells were scraped off and the plate system is centrifuged for 5 minutes at 1000 rpm in an IEC Centra-8R centrifuge. The filter screen was removed and the ChemoTx plate was inverted onto a 96 well plated with a funnel plate. The plate system was centrifuged for 5 minutes at 1000 pm. The volume in the wells was brought to 100 μl with medium and the plates were rested for approximately 20 minutes. The number of migrating cells was measured using the Cell Titer Glo Luminescent Assay from Promega (Madison, Wis.), and the TROPIX TR717 Microplate Luminometer (PE Applied Biosystems, Boston, Mass.)) by following the manufacturer's instructions.

Luciferase Replication Assay:

Plasmids encoding the full length genome of HIV-1 pNL-4-Luc with the gp 120 V-3 loop replaced by the Bgl II fragment of HIV-1 ADA, YU-2 or HxB (ADA-Luc-FL, YU-2-Luc-FL and HxB-Luc-FL) were obtained from Dr. Susan Pontow (Washington University, St. Louis Mo.). Replication-competent luciferase reporter virus stocks were generated by transfection of plasmids into 293T cells using Superfect (Qiagen) or Mirus transfection reagents. Viral stocks were collected 48 hours following transfection and titered for luciferase production on U-87-CCR5 or CXCR4 cells. U87-CD4-CCR5 cells (104/well) were plated in 96-well cell culture plates and incubated overnight. Media was removed and replaced with 50 μl of fresh culture media (DMEM, 10% FCS) and 50 μl of compound diluted in culture medium. Cells were incubated with compound at 37° C. for 1 hour. The resultant supernatant was removed and replaced with 20 μl of media containing compound and infected with an equal volume of diluted or undiluted virus stock at 37° C. for 3-4 hours. The cells were washed once with DMEM, and 200 μl of media containing compound was added. The cultures were incubated for 3 days, the cells lysed in luciferase lysis buffer (Promega, Madison, Wis.) and transferred to Immulon plates (Dynex Technologies, Chantilly Va.). An equal volume of luciferase substrate (Promega, Madison Wis.) was added to lysates and the plates read immediately in a Wallac Luminometer. Fifty and ninety percent inhibitory concentrations were determined using GraphPad PRISM software.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound represented by the structural formula IA:

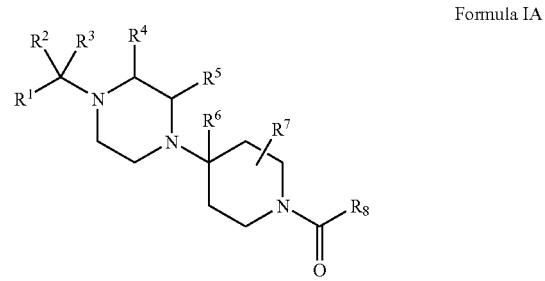

Formula IA or a pharmaceutically acceptable salt, or ester thereof; wherein:

$R^1$ is selected from the group consisting of $R^9$-phenyl, $R^9$-pyridyl, $R^9$-thiophenyl, $R^9$-naphthyl, and

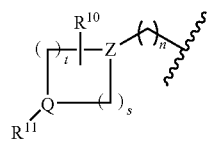

$R^2$ is selected from the group consisting of H and alkyl;

$R^3$ is selected from the group consisting of H, alkyl, alkoxyalkyl-, cycloalkyl, cycloalkylalkyl-, $R^9$-aryl, $R^9$-arylalkyl-, $R^9$-heteroaryl, and $R^9$-heteroarylalkyl-;

or $R^2$ and $R^3$ together are =O, =N($OR^{12}$), or =N—N($R^{13}$)($R^{14}$);

$R^4$, $R^5$, $R^6$ and $R^7$ are independently selected from the group consisting of H and alkyl;

$R^8$ is selected from the group consisting of

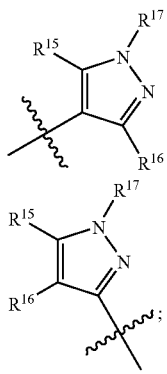
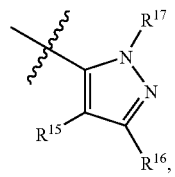 and
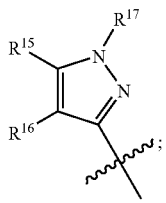

$R^9$ is 1, 2 or 3 substituents independently selected from the group consisting of H, halogen, alkyl, alkoxy, —$CF_3$, —$OCF_3$, $CH_3C(O)$—, —CN, $CH_3S(O_2)$—, $CF_3S(O_2)$—, —N($R^{18}$)($R^{19}$);

$R^{10}$ is selected from the group consisting of H and alkyl;

$R^{11}$ is selected from the group consisting of H, alkyl, fluoroalkyl-, $R^9$-arylalkyl-, $R^9$-heteroaryl-, alkyl, alkyl-S($O_2$)—, cycloalkyl-S($O_2$)—, fluoroalkyl-S($O_2$)—, $R^9$-aryl-S($O_2$)—, $R^9$-heteroaryl-S($O_2$)—, N($R^{18}$)($R^{19}$)-S($O_2$)—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

$R^{12}$ is H, alkyl, fluoroalkyl-, cycloalkylalkyl-, hydroxyalkyl-, alkyl-O-alkyl-, alkyl-O—C(O)-alkyl- or N($R^{18}$)($R^{19}$)—C(O)-alkyl-;

$R^{13}$ and $R^{14}$ are independently selected from the group consisting of H, alkyl and cycloalkyl, or $R^{13}$ and $R^{14}$ together are ($C_2$-$C_6$)alkylene and form a ring with the nitrogen atom to which they are shown attached;

$R^{15}$ and $R^{16}$ are independently selected from the group consisting of alkyl, halogen, —$NR^{18}R^{19}$, —OH, —$CF_3$, —$OCH_3$, —O-acyl and —$OCF_3$;

$R^{17}$ is $R^{20}$O—;

$R^{18}$ and $R^{19}$ are independently selected from the group consisting of H and alkyl;

$R^{20}$ is selected from the group consisting of alkyl, haloalkyl cycloalkyl, heterocyclyl, aralkyl, alkylaryl, aryl, and heteroaryl;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

2. The compound of claim 1, wherein:

$R^2$ is selected from the group consisting of H and ($C_1$-$C_6$)alkyl;

$R^3$ is selected from the group consisting of H, ($C_1$-$C_6$)alkyl, ($C_1$-$C_6$)alkoxy($C_1$-$C_6$)alkyl-, ($C_3$-$C_{10}$)cycloalkyl, ($C_3$-$C_{10}$)cycloalky($C_1$-$C_6$)lalkyl-, $R^9$-aryl, $R^9$-aryl($C_1$-$C_6$)alkyl-, $R^9$-heteroaryl, and $R^9$-heteroaryl($C_1$-$C_6$)alkyl-;

or $R^2$ and $R^3$ together are =O, =N($OR^{12}$), or =N—N($R^{13}$)($R^{14}$);

$R^4$, $R^5$, $R^6$ and $R^7$ are independently selected from the group consisting of H and ($C_1$-$C_6$)alkyl;

$R^8$ is selected from the group consisting of

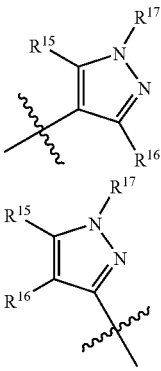
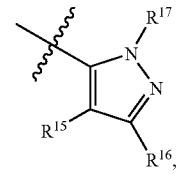 and
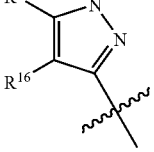

$R^9$ is 1, 2 or 3 substituents independently selected from the group consisting of H, halogen, ($C_1$-$C_6$)alkyl, ($C_1$-$C_6$)alkoxy, —$CF_3$, —$OCF_3$, $CH_3C(O)$—, —CN, $CH_3S(O_2)$—, $CF_3S(O_2)$—, —N($R^{18}$)($R^{19}$);

$R^{10}$ is selected from the group consisting of H and ($C_1$-$C_6$)alkyl;

$R^{11}$ is selected from the group consisting of H, ($C_1$-$C_6$)alkyl, fluoro($C_1$-$C_6$)alkyl-, $R^9$-aryl($C_1$-$C_6$)alkyl-, $R^9$-heteroaryl-, ($C_1$-$C_6$)alkyl, ($C_1$-$C_6$)alkyl-S($O_2$)—, ($C_3$-$C_6$)cycloalkyl-S($O_2$)—, fluoro($C_1$-$C_6$)alkyl-S($O_2$)—, $R^9$-aryl-S($O_2$)—, $R^9$-heteroaryl-S($O_2$)—, N($R^{18}$)($R^{19}$)—S($O_2$)—, ($C_1$-$C_6$)alkyl-C(O)—, ($C_3$-$C_6$)cycloalkyl-C(O)—, fluoro($C_1$-$C_6$)alkyl-C(O)—, $R^9$-aryl-C(O)—, ($C_1$-$C_6$)alkyl-NH—C(O)— and $R^9$-aryl-NH—C(O)—;

$R^{12}$ is H, ($C_1$-$C_6$)alkyl, fluoro($C_1$-$C_6$)alkyl-, ($C_3$-$C_{10}$)cycloalkyl($C_1$-$C_6$)alkyl-, hydroxy($C_1$-$C_6$)alkyl-, ($C_1$-$C_6$)alkyl-O—($C_2$-$C_6$)alkyl-, ($C_1$-$C_6$)alkyl-O—C(O)—($C_1$-$C_6$)alkyl- or N($R^{18}$)($R^{19}$)—C(O)—($C_1$-$C_6$)alkyl-;

$R^{13}$ and $R^{14}$ are independently selected from the group consisting of H, ($C_1$-$C_6$)alkyl and ($C_3$-$C_{10}$)cycloalkyl, or $R^{13}$ and $R^{14}$ together are ($C_2$-$C_6$)alkyl and form a ring with the nitrogen atom to which they are shown attached;

$R^{15}$ and $R^{16}$ are independently selected from the group consisting of ($C_1$-$C_6$)alkyl, halogen, —$NR^{18}R^{19}$, —OH, —$CF_3$, —$OCH_3$, —O-acyl and —$OCF_3$;

$R^{17}$ is $R^{20}$O—;

$R^{18}$ and $R^{19}$ are independently selected from the group consisting of H and ($C_1$-$C_6$)alkyl;

$R^{20}$ is selected from the group consisting of ($C_1$-$C_6$)alkyl, halo($C_1$-$C_6$)alkyl, ($C_3$-$C_{10}$)cycloalkyl, heterocyclyl, aryl($C_1$-$C_6$)alkyl, ($C_1$-$C_6$)alkylaryl, aryl, and heteroaryl;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

3. A compound in isolated and purified form, said compound represented by the structural formula IB:

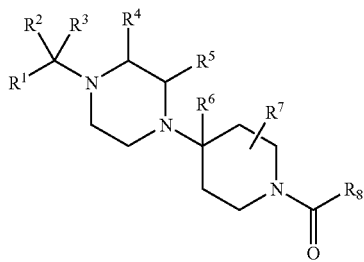

Formula IB or a pharmaceutically acceptable salt, solvate or ester thereof; wherein:

$R^1$ is selected from the group consisting of $R^9$-phenyl, $R^9$-pyridyl, $R^9$-thiophenyl, $R^9$-naphthyl, and

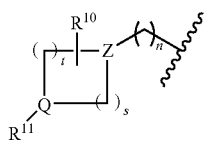

$R^2$ is selected from the group consisting of H and alkyl;

$R^3$ is selected from the group consisting of H, alkyl, alkoxyalkyl-, cycloalkyl, cycloalkylalkyl-, $R^9$-aryl, $R^9$-arylalkyl-, $R^9$-heteroaryl, and $R^9$-heteroarylalkyl-;

or $R^2$ and $R^3$ together are =O, =NOR$^{12}$, or =N—N($R^{13}$)($R^{14}$);

$R^4$, $R^5$, $R^6$ and $R^7$ are independently selected from the group consisting of H and alkyl;

$R^8$ is selected from the group consisting of

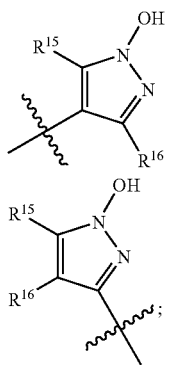
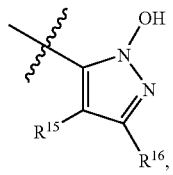

$R^9$ is 1, 2 or 3 substituents independently selected from the group consisting of H, halogen, alkyl, alkoxy, —CF$_3$, —OCF$_3$, CH$_3$C(O)—, —CN, CH$_3$S(O$_2$)—, CF$_3$S(O$_2$)—, —N(R$^{18}$)(R$^{19}$);

$R^{10}$ is selected from the group consisting of H and alkyl;

$R^{11}$ is selected from the group consisting of H, alkyl, fluoroalkyl-, $R^9$-arylalkyl-, $R^9$-heteroaryl-, alkyl, alkyl-S(O$_2$)—, cycloalkyl-S(O$_2$)—, fluoroalkyl-S(O$_2$)—, $R^9$-aryl-S(O$_2$)—, $R^9$-heteroaryl-S(O$_2$)—, N(R$^{18}$)(R$^{19}$)—S(O$_2$)—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

$R^{12}$ is H, alkyl, fluoroalkyl-, cycloalkylalkyl-, hydroxyalkyl-, alkyl-O-alkyl-, alkyl-O—C(O)-alkyl- or N(R$^{17}$)(R$^{18}$)—C(O)-alkyl-;

$R^{13}$ and $R^{14}$ are independently selected from the group consisting of H, alkyl and cycloalkyl, or $R^{13}$ and $R^{14}$ together are (C$_2$-C$_6$)alkyl and form a ring with the nitrogen atom to which they are shown attached;

$R^{15}$ and $R^{16}$ are independently selected from the group consisting of alkyl, halogen —NR$^{17}$R$^{18}$—OH, —CF$_3$, —OCH$_3$, —O-acyl and —OCF$_3$;

$R^{17}$ and $R^{18}$ are independently selected from the group consisting of H and alkyl;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

4. The compound of claim 3, wherein:

$R^2$ is selected from the group consisting of H and (C$_1$-C$_6$)alkyl;

$R^3$ is selected from the group consisting of H, (C$_1$-C$_6$)alkyl, (C$_1$-C$_6$)alkoxy(C$_1$-C$_6$)alkyl-, (C$_3$-C$_{10}$)cycloalkyl, (C$_3$-C$_{10}$)cycloalky(C$_1$-C$_6$)lalkyl-, $R^9$-aryl, $R^9$-aryl(C$_1$-C$_6$)alkyl-, $R^9$-heteroaryl, and $R^9$-heteroaryl(C$_1$-C$_6$)alkyl-;

or $R^2$ and $R^3$ together are =O, =N(OR$^{12}$), or =N—N(R$^{13}$)(R$^{14}$);

$R^4$, $R^5$, $R^6$ and $R^7$ are independently selected from the group consisting of H and (C$_1$-C$_6$)alkyl;

$R^8$ is selected from the group consisting of

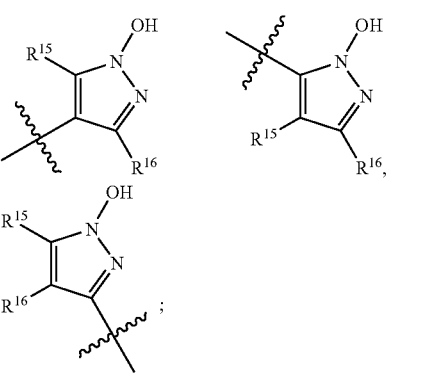

$R^9$ is 1, 2 or 3 substituents independently selected from the group consisting of H, halogen, (C$_1$-C$_6$)alkyl, (C$_1$-C$_6$)alkoxy, —CF$_3$, —OCF$_3$, CH$_3$C(O)—, —CN, CH$_3$S(O$_2$)—, CF$_3$S(O$_2$)—, —N(R$^{18}$)(R$^{19}$);

$R^{10}$ is selected from the group consisting of H and (C$_1$-C$_6$)alkyl;

$R^{11}$ is selected from the group consisting of H, (C$_1$-C$_6$)alkyl, fluoro(C$_1$-C$_6$)alkyl-, $R^9$-aryl(C$_1$-C$_6$)alkyl-, $R^9$-heteroaryl-, (C$_1$-C$_6$)alkyl, (C$_1$-C$_6$)alkyl-S(O$_2$)—, (C$_3$-C$_6$)cycloalkyl-S(O$_2$)—, fluoro(C$_1$-C$_6$)alkyl-S(O$_2$)—, $R^9$-aryl-S(O$_2$)—, $R^9$-heteroaryl-S(O$_2$)—, N(R$^{17}$)(R$^{18}$)—S(O$_2$)—, (C$_1$-C$_6$)alkyl-C(O)—, (C$_3$-C$_6$)cycloalkyl-C(O)—, fluoro(C$_1$-C$_6$)alkyl-C(O)—, $R^9$-aryl-C(O)—, (C$_1$-C$_6$)alkyl-NH—C(O)— and $R^9$-aryl-NH—C(O)—;

$R^{12}$ is H, (C$_1$-C$_6$)alkyl, fluoro(C$_1$-C$_6$)alkyl-, (C$_3$-C$_{10}$)cycloalkyl(C$_1$-C$_6$)alkyl-, hydroxy(C$_1$-C$_6$)alkyl-, (C$_1$-C$_6$)alkyl-O—(C$_2$-C$_6$)alkyl-, (C$_1$-C$_6$)alkyl-O—C(O)—(C$_1$-C$_6$)alkyl- or N(R$^{17}$)(R$^{18}$)—C(O)—(C$_1$-C$_6$)alkyl-;

R[13] and R[14] are independently selected from the group consisting of H, $(C_1-C_6)$alkyl and $(C_3-C_{10})$cycloalkyl, or R[13] and R[14] together are $(C_2-C_6)$alkyl and form a ring with the nitrogen atom to which they are shown attached;

R[15] and R[16] are independently selected from the group consisting of $(C_1-C_6)$alkyl, halogen, $-NR^{17}R^{18}$, $-OH$, $-CF_3$, $-OCH_3$, $-O$-acyl and $-OCF_3$;

R[17] and R[18] are independently selected from the group consisting of H and $(C_1-C_6)$alkyl;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

5. The compound of claim 1, wherein $R^1$ is $R^9$-phenyl.

6. The compound of claim 1, wherein $R^1$ is

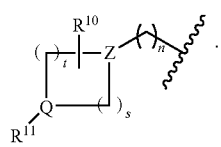

7. The compound of claim 6, wherein in Z is CH, and Q is N.

8. The compound of claim 1, wherein $R^2$ is hydrogen and $R^3$ is selected from the group consisting of $(C_1-C_6)$alkyl, $(C_1-C_6)$alkoxy$(C_1-C_6)$alkyl-, and $R^9$-aryl.

9. A compound selected from the group consisting of

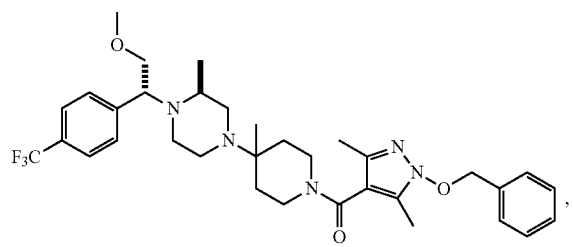

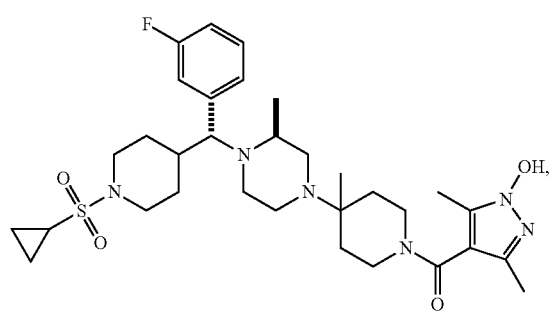

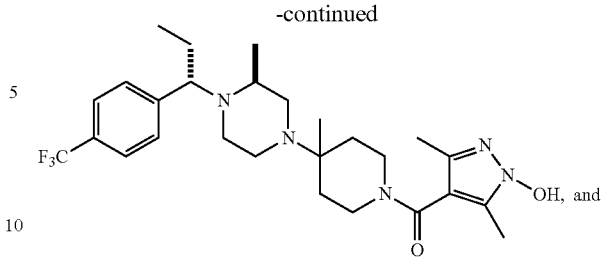

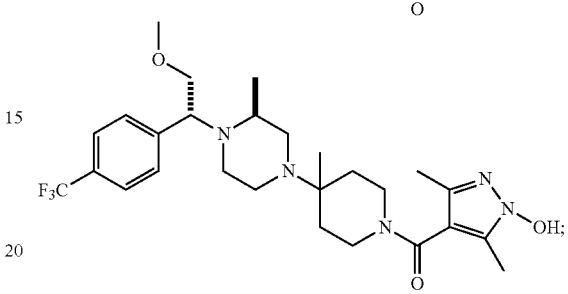

or a pharmaceutically acceptable salt thereof.

10. A pharmaceutical composition comprising a therapeutically effective amount of at least one compound of claim 1, or a pharmaceutically acceptable salt or ester thereof in combination with at least one pharmaceutically acceptable carrier.

11. The pharmaceutical composition of claim 10, additionally comprising one or more anti-viral agents useful in the treatment of Human Immuno-deficiency Virus.

12. The pharmaceutical composition of claim 11, wherein said antiviral agent is selected from the group consisting of nucleoside reverse transcriptase inhibitors, non-nucleoside reverse transcriptase inhibitors and protease inhibitors.

13. The pharmaceutical composition of claim 12 wherein said antiviral agent is selected from the group consisting of zidovudine, lamivudine, zalcitabine, didanosine, stavudine, abacavir, adefovir dipivoxil, lobucavir, BCH-10652, emitricitabine, beta-L-FD4, DAPD, lodenosine, nevirapine, delaviridine, efavirenz, PNU-142721, AG-1549, MKC-442, (+)-calanolide A and B, saquinavir, indinavir, ritonavir, nelfinavir, lasinavir, DMP-450, BMS-2322623, ABT-378, amprenavir, hydroxyurea, ribavirin, IL-2, IL-12, pentafuside, Yissum No. 11607 and AG-1549.

14. The pharmaceutical composition of claim 11, wherein said at least one compound of structural formula IA or a pharmaceutically acceptable salt or ester thereof and said one or more anti-viral agents are present in different dosage amounts or in fixed dosage amounts.

15. A kit comprising in separate containers in a single package pharmaceutical compositions for use in combination to treat Human Immunodeficiency Virus which comprises in one container a pharmaceutical composition comprising at least one compound of claim 1, or a pharmaceutically acceptable salt or ester thereof in one or more pharmaceutically acceptable carriers, and in a separate container, one or more pharmaceutical compositions comprising one or more antiviral agents useful in the treatment of Human Immunodeficiency Virus in one or more pharmaceutically acceptable carriers.

16. A process for preparing a compound represented by the structural formula IC:

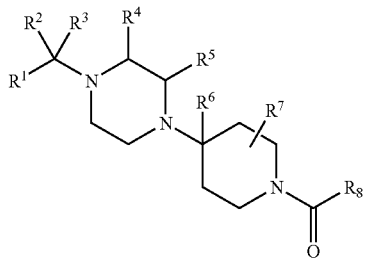

Formula IC or a pharmaceutically acceptable salt threrof; wherein:
$R^1$ is selected from the group consisting of $R^9$-phenyl, $R^9$-pyridyl, $R^9$-thiophenyl, $R^9$-naphthyl, and

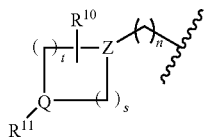

$R^2$ is selected from the group consisting of H and alkyl;
$R^3$ is selected from the group consisting of H, alkyl, alkoxyalkyl-, cycloalkyl, cycloalkylalkyl-, $R^9$-aryl, $R^9$-arylalkyl-, $R^9$-heteroaryl, and $R^9$-heteroarylalkyl-;
or $R^2$ and $R^3$ together are =O, =N(OR$^{12}$), or =N—N(R$^{13}$)(R$^{14}$);
$R^4$, $R^5$, $R^6$ and $R^7$ are independently selected from the group consisting of H and alkyl;
$R^8$ is selected from the group consisting of

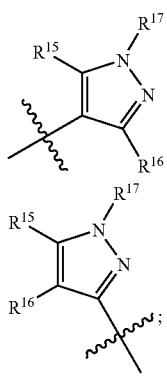 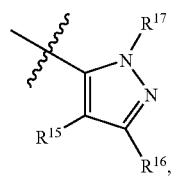

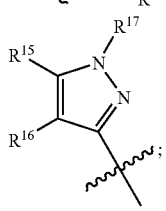;

$R^9$ is 1, 2 or 3 substituents independently selected from the group consisting of H, halogen, alkyl, alkoxy, —CF$_3$, —OCF$_3$, CH$_3$C(O)—, —CN, CH$_3$S(O$_2$)—, CF$_3$S(O$_2$)—, —N(R$^{18}$)(R$^{19}$);
$R^{10}$ is selected from the group consisting of H and alkyl;
$R^{11}$ is selected from the group consisting of H, alkyl, fluoroalkyl-, $R^9$-arylalkyl-, $R^9$-heteroaryl-, alkyl, alkyl-S(O$_2$)—, cycloalkyl-S(O$_2$)—, fluoroalkyl-S(O$_2$)—, $R^9$-aryl-S(O$_2$)—, $R^9$-heteroaryl-S(O$_2$)—, N(R$^{18}$)(R$^{19}$)—S(O$_2$)—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;

$R^{12}$ is H, alkyl, fluoroalkyl-, cycloalkylalkyl-, hydroxyalkyl-, alkyl-O-alkyl-, alkyl-O—C(O)-alkyl- or N(R$^{18}$)(R$^{19}$)—C(O)-alkyl-;
$R^{13}$ and $R^{14}$ are independently selected from the group consisting of H, alkyl and cycloalkyl, or $R^{13}$ and $R^{14}$ together are (C$_2$-C$_6$)alkylene and form a ring with the nitrogen atom to which they are shown attached;
$R^{15}$ and $R^{16}$ are independently selected from the group consisting of alkyl, halogen, —NR$^{18}$R$^{19}$, —OH, —CF3, —OCH$_3$, —O-acyl and —OCF$_3$;
$R^{17}$ is selected from the group consisting of R$^{20}$O— and R$^{20}$R$^{21}$N—;
$R^{18}$ and $R^{19}$ are independently selected from the group consisting of H and alkyl;
$R^{20}$ is selected from the group consisting of H, alkyl, haloalkyl cycloalkyl, heterocyclyl, aralkyl, alkylaryl, aryl, and heteroaryl;
$R^{21}$ is selected from the group consisting of H, alkyl, fluoro-alkyl-, $R^9$-arylalkyl-, $R^9$-heteroaryl-, alkyl, alkyl-S(O$_2$)—, cycloalkyl-S(O$_2$)—, fluoroalkyl-S(O$_2$)—, $R^9$-aryl-S(O$_2$)—, $R^9$-heteroaryl-S(O$_2$)—, N(R$^{18}$)(R$^{19}$)—S(O$_2$)—, alkyl-C(O)—, cycloalkyl-C(O)—, fluoroalkyl-C(O)—, $R^9$-aryl-C(O)—, alkyl-NH—C(O)— and $R^9$-aryl-NH—C(O)—;
Q and Z are independently selected from the group consisting of CH and N;
n is 0, 1, 2, 3 or 4;
s is 0, 1, 2, 3 or 4; and
t is 1, 2, 3 or 4;
with the proviso that when n is 0, Z is CH;
comprising reacting an amine of the formula

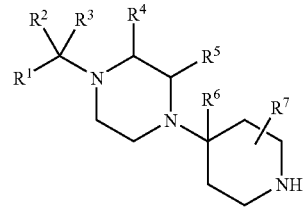

with a carboxylic acid of formula R$^8$COOH or an acid chloride of formula R$^8$C(O)Cl; wherein $R^1$-$R^8$ are as set forth for Formula IC.

17. The process of claim 16, wherein:
$R^2$ is selected from the group consisting of H and (C$_1$-C$_6$) alkyl;
$R^3$ is selected from the group consisting of H, (C$_1$-C$_6$)alkyl, (C$_1$-C$_6$)alkoxy(C$_1$-C$_6$)alkyl-, (C$_3$-C$_{10}$)cycloalkyl, (C$_3$-C$_{10}$)cycloalky(C$_1$-C$_6$)lalkyl-, $R^9$-aryl, $R^9$-aryl(C$_1$-C$_6$)alkyl-, $R^9$-heteroaryl, and $R^9$-heteroaryl(C$_1$-C$_6$)alkyl-;
or $R^2$ and $R^3$ together are =O, =N(OR$^{12}$), or =N—N(R$^{13}$)(R$^{14}$);
$R^4$, $R^5$, $R^6$ and $R^7$ are independently selected from the group consisting of H and (C$_1$-C$_6$)alkyl;
$R^8$ is selected from the group consisting of

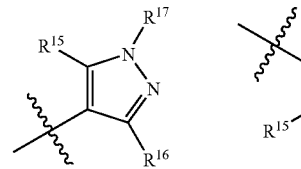 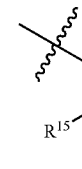 and

-continued

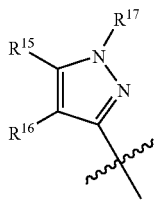

$R^9$ is 1, 2 or 3 substituents independently selected from the group consisting of H, halogen, $(C_1-C_6)$alkyl, $(C_1-C_6)$alkoxy, —$CF_3$, —$OCF_3$, $CH_3C(O)$—, —CN, $CH_3S(O_2)$—, $CF_3S(O_2)$—, —$N(R^{18})(R^{19})$;

$R^{10}$ is selected from the group consisting of H and $(C_1-C_6)$alkyl;

$R^{11}$ is selected from the group consisting of H, $(C_1-C_6)$alkyl, fluoro$(C_1-C_6)$alkyl-, $R^9$-aryl$(C_1-C_6)$alkyl-, $R^9$-heteroaryl-, $(C_1-C_6)$alkyl, $(C_1-C_6)$alkyl-S$(O_2)$—, $(C_3-C_6)$cycloalkyl-S$(O_2)$—, fluoro$(C_1-C_6)$alkyl-S$(O_2)$—, $R^9$-aryl-S$(O_2)$—, $R^9$-heteroaryl-S$(O_2)$—, $N(R^{18})(R^{19})$—S$(O_2)$—, $(C_1-C_6)$alkyl-C(O)—, $(C_3-C_6)$cycloalkyl-C(O)—, fluoro$(C_1-C_6)$alkyl-C(O)—, $R^9$-aryl-C(O)—, $(C_1-C_6)$alkyl-NH—C(O)— and $R^9$-aryl-NH—C(O)—;

$R^{12}$ is H, $(C_1-C_6)$alkyl, fluoro$(C_1-C_6)$alkyl-, $(C_3-C_{10})$cycloalkyl$(C_1-C_6)$alkyl-, hydroxy$(C_1-C_6)$alkyl-, $(C_1-C_6)$alkyl-O—$(C_2-C_6)$alkyl-, $(C_1-C_6)$alkyl-O—C(O)—$(C_1-C_6)$alkyl- or $N(R^{18})(R^{19})$—C(O)—$(C_1-C_6)$alkyl-;

$R^{13}$ and $R^{14}$ are independently selected from the group consisting of H, $(C_1-C_6)$alkyl and $(C_3-C_{10})$cycloalkyl, or $R^{13}$ and $R^{14}$ together are $(C_2-C_6)$alkyl and form a ring with the nitrogen atom to which they are shown attached;

$R^{15}$ and $R^{16}$ are independently selected from the group consisting of $(C_1-C_6)$alkyl, halogen, —$NR^{18}R^{19}$, —OH, —CF3, —$OCH_3$, —O-acyl and —$OCF_3$;

$R^{17}$ is selected from the group consisting of $R^{20}$O— and $R^{20}R^{21}$N—;

$R^{18}$ and $R^{19}$ are independently selected from the group consisting of H and $(C_1-C_6)$alkyl;

$R^{20}$ is selected from the group consisting of H, $(C_1-C_6)$alkyl, halo$(C_1-C_6)$alkyl, $(C_3-C_{10})$cycloalkyl, heterocyclyl, aryl$(C_1-C_6)$alkyl, $(C_1-C_6)$alkylaryl, aryl, and heteroaryl;

$R^{21}$ is selected from the group consisting of H, $(C_1-C_6)$alkyl, fluoro-$(C_1-C_6)$alkyl-, $R^9$-aryl$(C_1-C_6)$alkyl-, $R^9$-heteroaryl-, $(C_1-C_6)$alkyl, $(C_1-C_6)$alkyl-S$(O_2)$—, cyclo$(C_3-C_6)$alkyl-S$(O_2)$—, fluoro$(C_1-C_6)$alkyl-S$(O_2)$—, $R^9$-aryl-S$(O_2)$—, $R^9$-heteroaryl-S$(O_2)$—, $N(R^{18})(R^{19})$—S$(O_2)$—, $(C_1-C_6)$alkyl-C(O)—, $(C_3-C_6)$cycloalkyl-C(O)—, fluoro$(C_1-C_6)$alkyl-C(O)—, $R^9$-aryl-C(O)—, $(C_1-C_6)$alkyl-NH—C(O)— and $R^9$-aryl-NH—C(O)—;

Q and Z are independently selected from the group consisting of CH and N;

n is 0, 1, 2, 3 or 4;

s is 0, 1, 2, 3 or 4; and t is 1, 2, 3 or 4;

with the proviso that when n is 0, Z is CH.

18. The process of claim 16, wherein the reaction of the amine with the carboxylic acid or acid chloride is conducted in the presence of one or more amidation coupling agents.

19. The process of claim 18, wherein said amidation coupling agents comprise 1-hydroxybenzotriazole (HOBT) and 1-(3-dimethylaminopropyl)-3-ethyl carbodiimide hydrochloride (DEC).

20. A pharmaceutical composition comprising a therapeutically effective amount of at least one compound of claim 9, or a pharmaceutically acceptable salt thereof in combination with at least one pharmaceutically acceptable carrier.

* * * * *

UNITED STATES PATENT AND TRADEMARK OFFICE
CERTIFICATE OF CORRECTION

PATENT NO. : 7,659,275 B2  Page 1 of 1
APPLICATION NO. : 11/358520
DATED : February 9, 2010
INVENTOR(S) : Chan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this

Thirtieth Day of November, 2010

David J. Kappos
*Director of the United States Patent and Trademark Office*